(12) United States Patent
Roh et al.

(10) Patent No.: US 11,112,770 B2
(45) Date of Patent: Sep. 7, 2021

(54) SYSTEMS AND METHODS FOR ASSISTING A SURGEON AND PRODUCING PATIENT-SPECIFIC MEDICAL DEVICES

(71) Applicant: Carlsmed, Inc., Carlsbad, CA (US)

(72) Inventors: Jeffrey Roh, Seattle, WA (US); Justin Esterberg, Mercer Island, WA (US)

(73) Assignee: Carlsmed, Inc., Carlsbad, CA (US)

( * ) Notice: Subject to any disclaimer, the term of this patent is extended or adjusted under 35 U.S.C. 154(b) by 90 days.

(21) Appl. No.: 16/242,877

(22) Filed: Jan. 8, 2019

(65) Prior Publication Data
US 2019/0146458 A1    May 16, 2019

Related U.S. Application Data

(60) Provisional application No. 62/583,954, filed on Nov. 9, 2017.

(51) Int. Cl.
*G05B 19/4099*    (2006.01)
*G16H 50/20*    (2018.01)
(Continued)

(52) U.S. Cl.
CPC ......... *G05B 19/4099* (2013.01); *G16H 30/40* (2018.01); *G16H 50/20* (2018.01); *G16H 50/50* (2018.01); *G05B 2219/49007* (2013.01)

(58) Field of Classification Search
None
See application file for complete search history.

(56) References Cited

U.S. PATENT DOCUMENTS

| 4,704,686 A | 11/1987 | Aldinger |
| 6,696,073 B2 | 2/2004 | Boyce et al. |

(Continued)

FOREIGN PATENT DOCUMENTS

| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION satire series clinical application." Medical Now, No. 78; Aug. 2015, 4 pages.

(Continued)

*Primary Examiner* — Robert A Cassity
(74) *Attorney, Agent, or Firm* — Perkins Coie LLP

(57) ABSTRACT

Systems and methods for assisting a surgeon with implant during a surgery are disclosed. A method includes defining areas of interest in diagnostic data of a patient and defining an implant type. Post defining the areas of interest, salient points are determined for the areas of interest. Successively, an XZ angle, an XY angle, and a position entry point for an implant are determined based on the salient points of the areas of interest. In spinal procedures, a maximum screw diameter and a length of the spinal screw are successively determined based on the salient points. Based on determined length and diameter, a spinal screw and a matching screw guide is determined. Thereafter, the spinal screw and the screw guide is printed using a Three-Dimensional (3D) printer. Such printed spinal screw and screw guide could be used by the surgeon during the spinal surgery.

23 Claims, 15 Drawing Sheets

(51) Int. Cl.
  *G16H 30/40* (2018.01)
  *G16H 50/50* (2018.01)

(56) References Cited

U.S. PATENT DOCUMENTS

| | | | |
|---|---|---|---|
| 6,772,026 | B2 | 8/2004 | Bradbury |
| 6,978,188 | B1 | 12/2005 | Christensen |
| 7,174,282 | B2 | 2/2007 | Hollister et al. |
| 7,799,077 | B2 | 9/2010 | Lang |
| 8,246,680 | B2 | 8/2012 | Betz |
| 8,265,949 | B2 | 9/2012 | Haddad |
| 8,275,594 | B2 | 9/2012 | Lin |
| 8,337,507 | B2 | 12/2012 | Lang |
| 8,394,142 | B2 | 3/2013 | Bertagnoli |
| 8,457,930 | B2 | 6/2013 | Shroeder |
| 8,556,983 | B2 | 10/2013 | Bojarski et al. |
| 8,644,568 | B1 | 2/2014 | Hoffman |
| 8,735,773 | B2 | 5/2014 | Lang |
| 8,758,357 | B2 | 6/2014 | Frey |
| 8,781,557 | B2 | 7/2014 | Dean |
| 8,843,229 | B2 | 9/2014 | Vanasse |
| 8,855,389 | B1 | 10/2014 | Hoffman |
| 8,870,889 | B2 | 10/2014 | Frey |
| 9,198,678 | B2 | 12/2015 | Frey et al. |
| 9,208,558 | B2 | 12/2015 | Dean |
| 9,445,907 | B2 | 9/2016 | Meridew |
| 9,542,525 | B2 | 1/2017 | Arisoy et al. |
| 9,642,633 | B2 | 5/2017 | Frey et al. |
| 9,693,831 | B2 | 7/2017 | Mosnier et al. |
| 9,707,058 | B2 | 7/2017 | Bassett |
| 9,757,245 | B2 | 9/2017 | O'Neil et al. |
| 9,775,680 | B2 | 10/2017 | Bojarski et al. |
| 9,782,228 | B2 | 10/2017 | Mosnier et al. |
| 9,993,341 | B2 | 6/2018 | Vanasse |
| 10,292,770 | B2 | 5/2019 | Ryan |
| 10,390,958 | B2 | 8/2019 | Maclennan |
| 10,463,433 | B2 | 11/2019 | Turner et al. |
| 10,517,681 | B2* | 12/2019 | Roh ............... G16H 50/20 |
| 10,588,589 | B2* | 3/2020 | Bregman-Amitai ... A61B 6/505 |
| 10,902,944 | B1 | 1/2021 | Casey et al. |
| 2004/0171924 | A1* | 9/2004 | Mire ............... A61B 34/20 600/407 |
| 2005/0049590 | A1 | 3/2005 | Alleyne et al. |
| 2006/0009780 | A1* | 1/2006 | Foley ............... A61B 17/7083 606/99 |
| 2007/0276501 | A1 | 11/2007 | Betz et al. |
| 2008/0161680 | A1* | 7/2008 | von Jako ............... A61B 34/20 600/424 |
| 2008/0195240 | A1 | 8/2008 | Martin |
| 2011/0301710 | A1 | 12/2011 | Mather et al. |
| 2012/0084064 | A1 | 4/2012 | Dzenis et al. |
| 2012/0191192 | A1 | 7/2012 | Park |
| 2012/0287238 | A1* | 11/2012 | Onishi ............... A61B 1/0005 348/45 |
| 2012/0296433 | A1 | 11/2012 | Farin |
| 2013/0211531 | A1 | 8/2013 | Steines et al. |
| 2014/0072608 | A1 | 3/2014 | Karagkiozaki et al. |
| 2014/0081659 | A1 | 3/2014 | Nawana et al. |
| 2014/0086780 | A1* | 3/2014 | Miller ............... A61F 2/30942 419/1 |
| 2014/0164022 | A1 | 6/2014 | Reed et al. |
| 2014/0350614 | A1* | 11/2014 | Frey ............... A61F 2/4611 606/86 R |
| 2015/0105891 | A1* | 4/2015 | Golway ............... G06F 30/00 700/98 |
| 2015/0324490 | A1* | 11/2015 | Page ............... G06Q 30/0621 700/98 |
| 2016/0015465 | A1 | 1/2016 | Steines et al. |
| 2016/0074048 | A1 | 3/2016 | Pavlovskaia et al. |
| 2016/0117817 | A1 | 4/2016 | Seel |
| 2016/0143744 | A1 | 5/2016 | Bojarski et al. |
| 2016/0210374 | A1 | 7/2016 | Mosnier et al. |
| 2016/0217268 | A1 | 7/2016 | Otto et al. |
| 2016/0300026 | A1* | 10/2016 | Bogoni ............... G16H 50/20 |
| 2016/0354039 | A1 | 12/2016 | Soto et al. |
| 2016/0378919 | A1 | 12/2016 | McNutt et al. |
| 2017/0000566 | A1* | 1/2017 | Gordon ............... A61B 34/10 |
| 2017/0014169 | A1 | 1/2017 | Dean et al. |
| 2017/0035514 | A1 | 2/2017 | Fox et al. |
| 2017/0061375 | A1 | 3/2017 | Laster et al. |
| 2017/0068792 | A1 | 3/2017 | Reiner |
| 2017/0135706 | A1 | 5/2017 | Frey et al. |
| 2017/0143494 | A1* | 5/2017 | Mahfouz ............... A61F 2/34 |
| 2017/0143831 | A1 | 5/2017 | Varanasi et al. |
| 2017/0220740 | A1 | 8/2017 | D'Urso |
| 2017/0252107 | A1* | 9/2017 | Turner ............... G06N 5/04 |
| 2017/0262595 | A1 | 9/2017 | Vorhis et al. |
| 2017/0367645 | A1* | 12/2017 | Klinder ............... A61B 5/4566 |
| 2018/0116727 | A1* | 5/2018 | Caldwell ............... G16H 50/50 |
| 2018/0168499 | A1 | 6/2018 | Bergold et al. |
| 2018/0168731 | A1 | 6/2018 | Reid et al. |
| 2018/0185075 | A1 | 7/2018 | She |
| 2018/0233222 | A1* | 8/2018 | Daley ............... A61B 8/0875 |
| 2018/0233225 | A1 | 8/2018 | Experton et al. |
| 2018/0250075 | A1* | 9/2018 | Cho ............... A61B 34/10 |
| 2018/0303552 | A1 | 10/2018 | Ryan |
| 2018/0338841 | A1 | 11/2018 | Miller et al. |
| 2019/0029757 | A1* | 1/2019 | Roh ............... G16H 50/00 |
| 2019/0146458 | A1 | 5/2019 | Roh et al. |
| 2019/0167435 | A1 | 6/2019 | Cordonnier |
| 2019/0201106 | A1* | 7/2019 | Siemionow ............... A61B 6/5235 |
| 2019/0262084 | A1* | 8/2019 | Roh ............... A61B 34/20 |
| 2019/0282367 | A1 | 9/2019 | Casey et al. |
| 2019/0321193 | A1 | 10/2019 | Casey et al. |
| 2020/0078180 | A1 | 3/2020 | Casey et al. |
| 2020/0085509 | A1* | 3/2020 | Roh ............... G16H 40/63 |
| 2020/0170802 | A1 | 6/2020 | Casey et al. |
| 2021/0059822 | A1 | 3/2021 | Casey et al. |

FOREIGN PATENT DOCUMENTS

| | | |
|---|---|---|
| CN | 204468348 U | 7/2015 |
| CN | 105796214 A | 7/2016 |
| WO | 2010151564 A1 | 12/2010 |
| WO | 2019112917 A1 | 6/2019 |

OTHER PUBLICATIONS

International Searching Authority, International Search Report and Written Opinion, PCT Patent Application PCT/US2018/063530, dated Feb. 12, 2019, 16 pages.
Materialise Mimics, "Efficiently turn scans into accurate virtual 3D models," <www.materialize.com/en/medical/software/mimics>, 1 page.
Pimenta, Dr. Luiz, "Current Surgical Strategies to Restore Proper Sagittal Alignment," Journal of Spine 2015, vol. 4, Issue 4, 2 pages.
International Search Report and Written Opinion for International Application No. PCT/US19/50885, dated Jan. 28, 2020 (21 pages).
International Search Report and Written Opinion for International Application No. PCT/US19/63855, dated Feb. 14, 2020 (15 pages).
U.S. Appl. No. 15/958,409 for Ryan, filed Apr. 21, 2017.

\* cited by examiner

| Screw Type and Size | Thread Diameter, $d_1$ | Core Diameter, $d_S$ | Crest Width, e | Thread Pitch, P | Leading Edge Radius, $r_4$ | Trailing Edge Radius, $r_5$ | Leading Edge Angle, $\alpha$ | Trailing Edge Angle, $\beta$ |
|---|---|---|---|---|---|---|---|---|
| HA 1.5 | 1.50 +0.00 / -0.15 | 1.10 +0.00 / -0.10 | 0.1 | 0.5 | 0.3 | 0.1 | 35 | 3 |
| HA 2.0 | 2.00 +0.00 / -0.15 | 1.30 +0.00 / -0.10 | 0.1 | 0.6 | 0.4 | 0.1 | 35 | 3 |
| HA 2.7 | 2.70 +0.00 / -0.15 | 1.90 +0.00 / -0.15 | 0.1 | 1.0 | 0.6 | 0.2 | 35 | 3 |
| HA 3.5 | 3.50 +0.00 / -0.15 | 2.40 +0.00 / -0.15 | 0.1 | 1.25 | 0.8 | 0.2 | 35 | 3 |
| HA 4.0 | 4.00 +0.00 / -0.15 | 2.90 +0.00 / -0.15 | 0.1 | 1.5 | 0.8 | 0.2 | 35 | 3 |
| HA 4.5 | 4.50 +0.00 / -0.15 | 3.00 +0.00 / -0.15 | 0.1 | 1.75 | 1.0 | 0.3 | 35 | 3 |
| HA 5.0 | 5.00 +0.00 / -0.15 | 3.50 +0.00 / -0.15 | 0.1 | 1.75 | 1.0 | 0.3 | 35 | 3 |

SYSTEMS AND METHODS FOR ASSISTING A SURGEON AND PRODUCING PATIENT-SPECIFIC MEDICAL DEVICES

CROSS-REFERENCE TO RELATED APPLICATION

This application claims priority to U.S. Provisional Patent Application No. 62/583,954, filed on Nov. 9, 2017 titled "SYSTEMS AND METHODS OF ASSISTING A SURGEON WITH SCREW PLACEMENT DURING A SPINAL SURGERY," which is herein incorporated by reference in its entirety.

TECHNICAL FIELD

The present disclosure is generally related to providing surgical assistance to a surgeon, and more particularly for providing medical devices and surgical assistance for a surgical procedure.

BACKGROUND

Assessing anatomical features of patient can help a physician perform a surgical procedure. For example, identifying and assessing a spinal deformity is of tremendous importance for a number of disorders affecting human spine. A pedicle is a dense stem-like structure that projects from the posterior of a vertebra. There are two pedicles per vertebra that connect to structures like a lamina and a vertebral arch. Conventionally available screws, used in spinal surgeries, are poly-axial pedicle screws made of titanium alloy. Titanium is chosen as it is highly resistant to corrosion and fatigue, and is more compatible with MRI imaging. Unfortunately, conventional spine kits with standard screw guides and pedicle screws may not be designed for use with abnormal vertebrae.

Pedicle screws were originally placed via a free-hand technique. Surgeons performing spinal surgeries merely rely on their experience and knowledge of known specific paths for performing the spinal surgeries. The free-hand techniques used by spinal surgeons rely on spinal anatomy of a patient. The spinal surgeon relies on pre-operative imaging and intra-operative anatomical landmarks for performing the spinal surgery. Assistive fluoroscopy and navigation are helpful in that they guide pedicle screw placement more or less in a real time, but are limited by time and costs involved in fluoroscopy, and significant radiation exposure during fluoroscopy.

Prior prefabricated screw guide insertion methods rely on the patient's diagnostics images. The diagnostics images are studied and a needle mark is made in a surgery film. Thereafter, a screw insertion point and an approach angle for drilling into the spine are determined. Such procedure may lead to several complications. For example, a lateral breach may occur, as shown in FIG. 1A of prior art. The pedicle screw may exit the wall of the vertebra and thus may compromise integrity of the surgery, which may lead to further medical complexities. Further, a medial breach may also occur, as shown in FIG. 1B of prior art. The pedicle screw may come close to or may come in contact with the central nervous system present in the spine, thus leading to medical complexities. Some complications of pedicle screws include (a) mal-positioning of the screw (medial wall breach, intra-foraminal placement, and sacroiliac joint violation), (b) fracture of the pedicle, (c) injury to the cord or nerve roots, and (d) fracture of the implant.

An accurate placement of the pedicle screw in the spine is illustrated in FIG. 1C of prior art. The approach entirely relies on experience of the surgeon and involves a lot of risk. Also, locating the appropriate pedicle screw for the screw guide is a painstaking task for the surgeon. Additionally, standard pedicle screws may be not suitable for the patient's anatomy. Improper placement and improper sizing of pedicle screws can lead to significant problems.

Thus, an efficient mechanism for providing assistance to a surgeon in screw placement during a spinal procedure and patient-specific surgical systems are much desired. Patient-specific medical technology can also help the assist the surgeon and improve outcomes.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Figure 2:
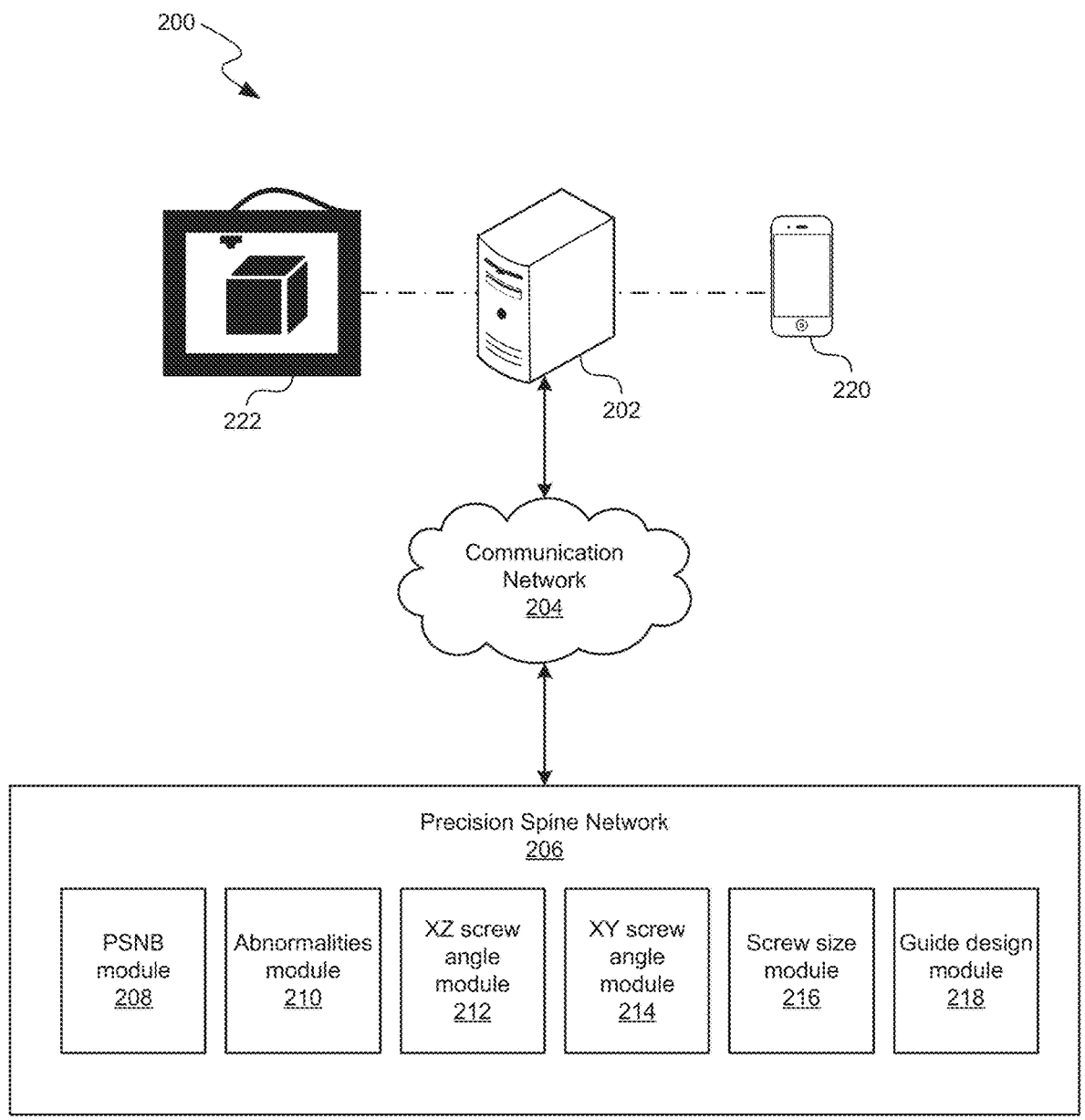
FIG. 2 illustrates a network connection diagram of a system for providing assistance to a surgeon during a spinal surgery, according to an embodiment.

FIG. 2 illustrates a network connection diagram or system 200 of a system 202 for providing assistance to a surgeon, according to an embodiment. The system 202 can provide assistance to a surgeon by, for example, providing patient-specific surgical information, surgical plans, technology recommendations (e.g., implant/instrument recommendations), and/or medical devices themselves. The surgeon can perform surgery based on output from the system 202. The output can include surgical information for manufacturing medical devices, including patient-specific implants, delivery instruments, etc., used in the procedure.

Manufacturing can be performed on site or off site. On-site manufacturing can reduce the number of sessions with a patient and/or the time to be able to perform the surgery whereas off-site manufacturing can be useful make the complex devices. Off-site manufacturing facilities may have specialized manufacturing equipment. In some cases, complicated components of a surgical kit can be manufactured off site while simpler components can be manufactured on site.

The system 200 can produce patient-specific technology tailored for the patient's anatomy to ensure proper treatment. A patient-specific surgical plan can include an entire surgical technique or portions thereof. Additionally, patient-specific devices can be designed for the surgical plan. This allows components of the patient-specific technology to be specifically designed for one another. The progress of treatment can be monitored over a period of time to help update the system 200. In trainable systems 200, post-treatment data can be used to train machine learning programs for developing surgical plans, patient-specific technology, or combinations thereof. Surgical plans can provide one or more characteristics of the at least one medical device, surgical techniques, imaging techniques, etc.

Figure 1A:
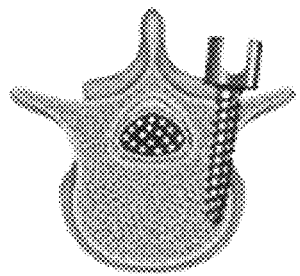
FIG. 1A illustrates lateral breach of a spinal screw in spine, according to prior art.
Figure 1B:
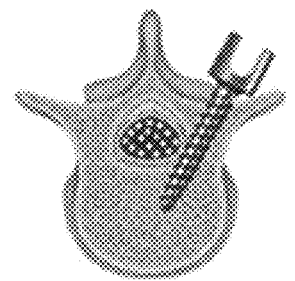
FIG. 1B illustrates medial breach of a spinal screw in spine, according to prior art.
Figure 1C:
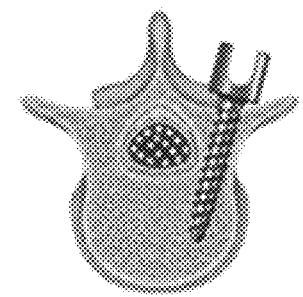
FIG. 1C illustrates accurate placement of a spinal screw in spine, according to prior art.

The system 200 of FIG. 2 can be used to produce treatment plans and patient-specific devices, whether for use with a robot or a physician, that was designed for the procedure to be performed. This allows for treatment flexibility. In robotic-assisted procedures, the robotic instructions from the system 200 can be used to control to a robotic apparatus (e.g., robotic surgery systems, navigation systems, etc.) for an implant surgery or by generating suggestions for medical device configurations to be used in surgery. In some procedures, both manual and robotic procedures can be performed. For example, one step of a surgical procedure can be manually performed by a surgeon and another step of the procedure can be performed by a robotic apparatus. Additionally, patient-specific components can be used with standard components made by the system 200. For example, in a spinal surgery, a pedicle screw kit can include both standard components and patient-specific customized components. For example, the implants (e.g., screws, screw holders, rods, etc.) can be designed and manufactured for the patient and the instruments can be standard instruments. This allows the components that are implanted to be designed and manufactured based on the patient's anatomy, and/or surgeon's preferences to enhance treatment. The patient-specific devices can improve, without limitation, delivery into the patient's body, placement at the treatment site, and interaction with the patient's anatomy. For example, embodiments of the system can be used to produce pedicle screws and components to avoid the problems discussed in connection with FIGS. 1A and 1B, as well as other problems.

With continued reference to FIG. 2, the system 202 may be connected to a communication network 204. The communication network 204 may further be connected with a precision spine network 206 for allowing data transfer between the system 202 and the precision spine network 206.

The communication network 204 may be a wired and/or a wireless network. The communication network 204, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and other communication techniques known in the art.

In one embodiment, the precision spine network 206 may be implemented as a facility over "the cloud" and may include a group of modules. The group of modules may include a Precision Spine Network Base (PSNB) module 208, an abnormalities module 210, an XZ screw angle module 212, an XY screw module 214, a screw size module 216 and a guide design module 218.

The PSNB module 208 may be configured to store images of patients and types of spinal screws, required in spinal surgeries. In some implementations, a similar module can be used for other types of surgeries to, for example, store patient data, device information, etc. While the PSNB is referred to below, in each instance other similar modules can be used for other types of surgeries. For example, a Precision Knee Network Based can be used to assist in anterior cruciate ligament (ACL) replacement surgeries. The images may be any of camera images, Magnetic Resonance Imaging (MRI) images, ultrasound images, Computerized Aided Tomography (CAT) scan images, Positron Emission Tomography (PET) images, and X-Ray images. In one case, the images may be analyzed to identify anatomical features, abnormalities, and salient features in the images, for performing spinal surgeries on the patients. In some implementations, the PSNB module 208 can store additional implant surgery information, such as patient information, (e.g., sex, age, height, weight, type of pathology, occupation, activity level, tissue information, health rating, etc.), specifics of implant systems (e.g., types and dimensions), availability of available implants, aspects of a surgeon's preoperative plan (e.g., surgeon's initial implant configuration, detection and measurement of the patient's anatomy on images, etc.), etc. In some implementations, the PSNB module 208 can convert the implant surgery information into formats useable for implant suggestion models and algorithms. For example, the implant surgery information can be tagged with particular identifiers for formulas or can be converted into numerical representations suitable for supplying to a machine learning model.

The abnormalities module 210 may measure distances between a number of salient features of one vertebra with salient features of another vertebra, for identifying disk pinches or bulges. Based on the identified disk pinches or bulges, herniated disks may be identified in the patients. It should be obvious to those skilled in the art, that given a wide variety of salient features and geometric rules, many spinal abnormalities could be identified. If the spinal abnormalities are identified, the PSNB module 208 may graphically identify areas having the spinal abnormalities and may send such information to a user device 220.

In one embodiment, information related to spinal surgeries may be displayed through a Graphical User Interface (GUI) of the user device 220, as illustrated using FIG. 2 smart phone. Further, the user device 220 may be any other device comprising a GUI, for example, a laptop, desktop, tablet, phablet, or other such devices known in the art.

The XZ screw angle module 212 may determine an XZ angle of a spinal screw or other implant to be used during the surgery. Further, the XY screw module 214 may determine an XY angle of the implant. The XZ screw angle module 212 and the XY screw angle module 214 may determine a position entry point for at least one spinal screw. The XZ screw angle module 212 and the XY screw module 214 may graphically represent the identified data and may send such information to the user device 220.

The screw size module 216 may be used to determine a screw diameter (e.g., a maximum screw diameter, minimum screw diameter, etc.) and/or a length of the screw based on the salient features identified from the images of the patients.

In some implementations, the XZ screw angle module 212, the XY screw angle module 214, and the screw size module 216 can identify implant configurations for other types of implants in addition to, or other than screws (e.g., pedicle screws, facet screws, etc.) such as cages, plates, rods, disks, fusions devices, spacers, rods, expandable devices, stents, etc. In addition, these modules may suggest implant configurations in relation to references other than an X, Y, Z, coordinate system. For example, in a spinal surgery, the suggestions can be in reference to the sagittal plane, mid-sagittal plane, coronal plane, frontal plane, or transverse plane. As another example, in an ACL replacement surgery, the suggestions can be an angle for a tibial tunnel in reference to the frontal plane of the femur. In various implementations, the XZ screw angle module 212, the XY screw angle module 214, or screw size module 216 can identify implant configurations using machine learning modules, algorithms, or combinations thereof, as described below in relation to FIGS. 10A-13.

The guide design module 218 may examine patient data to create a virtual model, topographical map, or representation of the patient's body, or portion thereof, such as the back or spine. Further, a position entry point may be retrieved to identify the spinal screws path through a screw guide, and holes large enough to accommodate the selected spinal screws into a Three-Dimensional (3D) design of the screw guide. Other design modules 218 can be utilized to provide other types of components. By way of example, the guide design module 218 can be designed to examine patient information to determine a surgical plan, design delivery instruments (e.g., screw guides, cannulas, ports, or the like), or other information or programs. As such, the precision network 206 can be adapted or modified to perform a wide range of procedures.

In one embodiment, information related to spinal surgeries may be used to print the spinal screw and the screw guide, based on the identified data. The spinal screw and the screw guide may be manufactured using, for example, a printed using a manufacturing system 222. The manufacturing system 22 can be a three-Dimensional (3D) printer. The 3D printer may be any general purpose 3D printer utilizing technologies such as Stereolithography (SLA), Digital Light Processing (DLP), Fused Deposition Modeling (FDM), Selective Laser Sintering (SLS), Selective laser melting (SLM), Electronic Beam Melting (EBM), Laminated object manufacturing (LOM) or the like. Other types of manufacturing devices can be used. The 3D printers can manufacture based on 3D fabrication data. The 3D fabrication data can include CAD data, 3D data, digital blueprints, stereolithography, or other data suitable for general purpose 3D printers. For example, the manufacturing system 222 can include a milling machine, a waterjet system, or combinations thereof, thereby providing manufacturing flexibility. The precision network 206 can output information suitable for the manufacturing system 222. In some embodiments, the precision network 206 provides CAD models, manufacturing programs or instructions, or other data for instructing the system 222. The system 202 can convert the CAD model to manufacturing data. In other embodiments, the manufacturing system 222 receives patient information from the system 202 and can generate, for example, CAD models, virtual models, tool paths, instruction sets, or the like for manufacturing. The system 222 can include components of the system 202 discussed in connection with FIG. 3 or the system 452 discussed in connection with FIG. 4.

Figure 3:
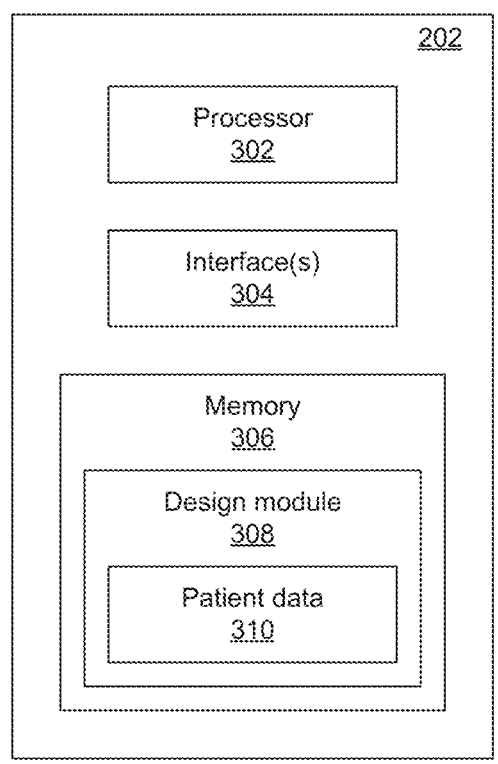
FIG. 3 illustrates a block diagram showing different components of the system for providing assistance to a surgeon, according to an embodiment.

Referring to FIG. 3, a block diagram showing different components of the system 202 is explained. The system 202 includes a processor 302, interface(s) 304, and a memory 306. The processor 302 may execute an algorithm stored in the memory 306 for augmenting an implant surgery, e.g., by providing assistance to a surgeon during a spinal surgery or other implant surgery, by providing controls to a robotic apparatus (e.g., robotic surgery systems, navigation system, etc.) for an implant surgery or by generating suggestions (e.g., labeled images, visual representations, surgical technique instructions, etc.) for implant configurations to be used in an implant surgery. The memory 306 can include computer-readable storage medium storing instructions that, when executed by the processor 302, cause the system 202 to perform operations. The processor 302 may also be configured to decode and execute any instructions received from one or more other electronic devices or server(s). The processor 302 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 302 may be configured to execute one or more computer-readable program instructions, such as program instructions to carry out any of the functions described in this description.

The interface(s) 304 may help a user to interact with the system 202. The user may be any of an operator, a technician, a doctor, and a doctor's assistant, or another automated system controlled by the system 202. The interface(s) 304 of the system 202 may either accept an input from the user or provide an output to the user, or may perform both the actions. The interface(s) 304 may either be a Command Line Interface (CLI), Graphical User Interface (GUI), or a voice interface.

The memory 306 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

The memory 306 may include modules, implemented as programmed instructions executed by the processor 302. In one case, the memory 306 may include a design module 308 for receiving information from the abnormalities module. The design module 308 may poll the surgeon for an information request. The design module 308 may allow the surgeon to design the implant and change the generated implant configurations, such as the entry point (e.g., entry point into the patient, entry points into a vertebra, entry points to the implantation site, etc.), and screw or other implant angles in any of various planes. If the surgeon changes the entry point or angles, the system can automatically update other features of the implant configuration to account for the changes, such as the implant dimensions (e.g., screw diameter, thread pitch, or length). The design module 308 may include patient data 310. The patient data 310 may include images of patients and may allow the surgeon to identify the patients. A patient may refer to a person on whom and operations is to be performed. The patient data 310 may include images of patients, received from a user device, such as the user device 220.

The design module 308 can be configured to allow the surgeon to design a wide range of implants. In a stent design module 308, a surgeon can select a type of stent based on the region of the vascular system to be treated. The system 202 can generate a suggested a stent configuration based on the patient data, surgeon preferences, or combinations thereof. The surgeon can change the suggested stent, including stent type, stent dimensions, stent features (e.g., anchors, eluting agents, etc.), delivery path (e.g., percutaneous delivery paths, open delivery paths, etc.), or the like. Other types of design modules 308 can be used.

Figure 4:
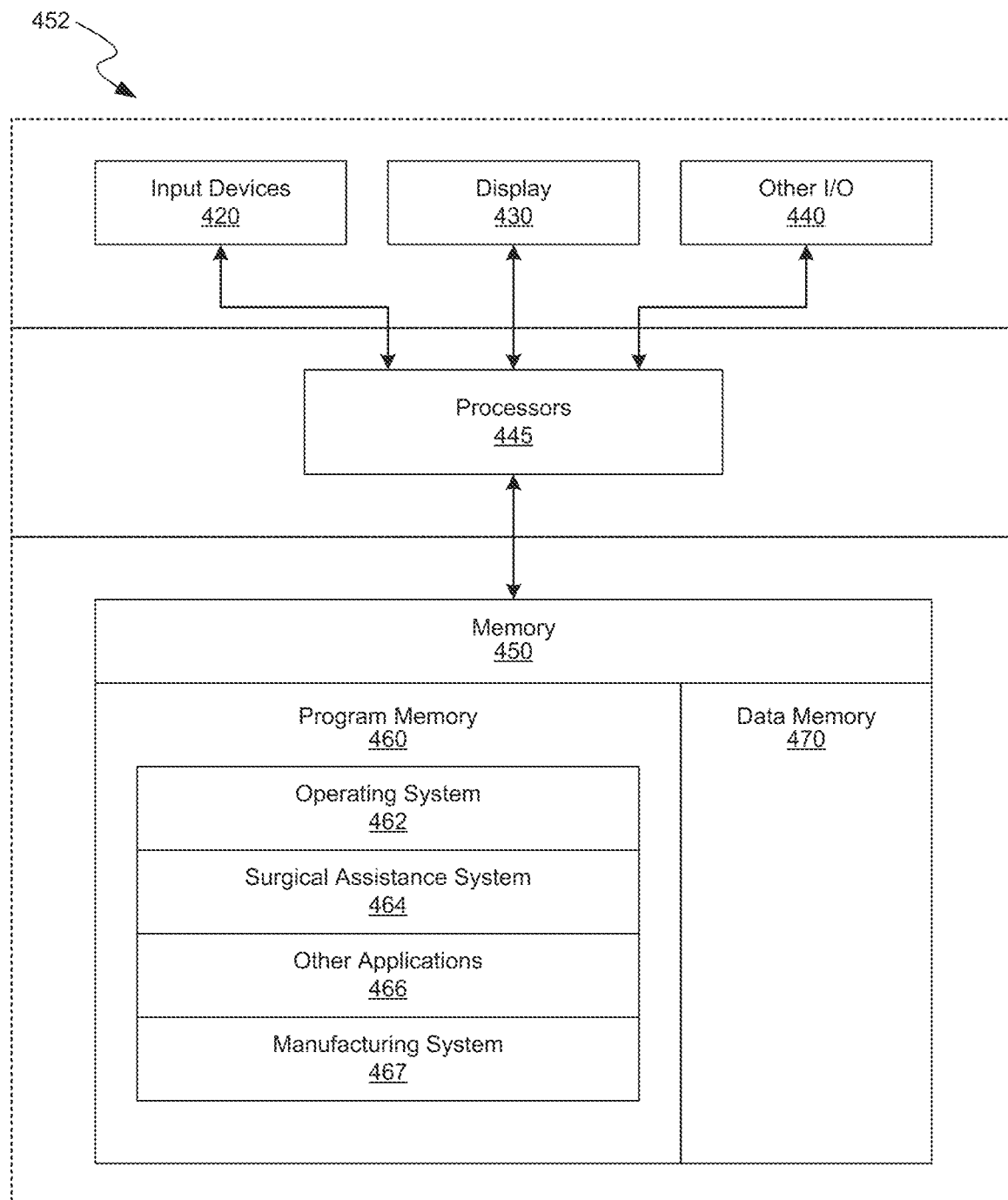
FIG. 4 illustrates a system for providing assistance prior to or during a surgical surgery, according to an embodiment.

FIG. 4 illustrates a system 452 for providing assistance prior to or during an implant surgery, according to an embodiment. The system 452 can improve surgeries that involve implants by one or more of guiding selection and manufacturing of implants, delivery instruments, navigation tools, or the like. The system 452 can comprise hardware components that improve surgeries using, for example, a surgical assistance system 464. In various implementations, the surgical assistance system 464 can obtain implant surgery information, convert the implant surgery information into a form compatible with an analysis procedure, apply the analysis procedure to obtain results, and use the results to provide a configuration for the implant surgery. The surgical assistance 464 can assist with a manufacturing of the implants, instruments, guides, and/or navigation tools.

The system 452 can determine an implant configuration, which can include characteristics, such as dimensions, materials, application features (e.g., implant sizes, implant functionality, anchoring features, suture type, etc.), and/or aspects of applying the implant such as insertion point, delivery path, implant position/angle, rotation, amounts of force to apply (e.g., torque applied to a screw, rotational speed of a screw, rate of expansion of expandable implants, and so forth), etc. A patient-specific implant can be manufactured based, at least in part, on the implant configuration selected for the patient. Each patient can receive an implant that is specifically designed for their anatomy. In some procedures, the system 452 can handle the entire design and manufacturing process. In other embodiments, a physician can alter the implant configuration for further customization. An iterative design process can be employed in which the physician and system 452 work together. For example, the system 452 can generate a proposed patient-specific implant. The physician can identify characteristics of the implant to be changed and can input potential design changes. The system 452 can analyze the feedback from the physician to determine a refined patient-specific implant design and to produce a patient-specific model. This process can be repeated any number of times until arriving at a suitable design. Once approved, the implant can be manufactured based on the selected design.

The stored implant surgery information can include images of a target area, such as MRI scans of a spine, patient information such as sex, weight, etc., virtual models of the target area, a databased of technology models (e.g., CAD models), or a surgeon's pre-operative plan. The surgical assistance system 464 can convert the implant surgery information, for example, by converting images into arrays of integers or histograms, entering patient information into feature vectors, or extracting values from the pre-operative plan.

In some implementations, surgical assistance system 464 can analyze data (e.g., one or more images) of a patient to identify one or more features of interest. The features of interest can include, without limitation, implantation sites, targeted features, non-targeted features, access paths, anatomical structures, or combinations thereof. The implantation sites can be determined based upon one or more of risk factors, patient information, surgical information, or combinations thereof. The risk factors can be determined by the surgical assistant system based upon the patient's medical history. For example, if the patient is susceptible to infections, the surgical assistant system 464 can recommend a minimally invasive procedure whereas the surgical assistant system may recommend open procedure access paths for patients less susceptible to infection. In some implementations, the physician can provide the risk factors before or during the procedure. Patient information can include, without limitation, patient sex, age, bone density, health rating, or the like. The surgical information can include available navigation systems, robotic surgery platforms, access tools, surgery kits, or the like.

In some implementations, the surgical assistance system 464 can apply analysis procedures by supplying the converted implant surgery information to a machine learning model trained to select implant configurations. For example, a neural network model can be trained to select pedicle screw configurations for a spinal surgery. The neural network can be trained with training items each comprising a set of images scans (e.g., camera, MRI, CT, x-ray, etc.) and patient information, an implant configuration used in the surgery, and/or a scored surgery outcome resulting from one or more of: surgeon feedback, patient recovery level, recovery time, results after a set number of years, etc. This neural network can receive the converted surgery information and provide output indicating the pedicle screw configuration. Analysis procedures can be used to select the types of implants, instruments, surgical techniques, etc.

In other implementations, the surgical assistance system 464 can apply the analysis procedure by A) localizing and classifying a surgery target, B) segmenting the target to determine boundaries, C) localizing optimal implant insertion points, D) identifying target structures (e.g., pedicles and isthmus), and/or computing implant configurations based on results of A-D. Additionally or alternatively, the surgical assistance system 464 can generate one or more 3D models (e.g., CAD models, virtual models, etc.) for manufacturing implants, delivery instruments, guides, or the like. The 3D models can represent the patient's anatomy, implants, candidate models, etc. The surgical assistance system 464 can determine whether a candidate medical device falls within specified parameters based on the 3D image of at least part of the patient and the salient features. In response to the determining, the candidate medical device is selected. The specified parameters can be selected by the surgical assistance system 464, surgeon, or combinations thereof. Neural networks can be trained to generate and/or modify models, as well as other data, including manufacturing information (e.g., data, algorithms, etc.).

The surgical assistance system 464 can apply the analysis procedure by building a virtual model of a surgery target area suitable for manufacturing surgical items. For example, the surgical assistance system 464 can also localize and classify areas of interest within the virtual model, segmenting areas of interest, localizing insertion points, and computing implant configurations by simulating implant insertions in the virtual model. Each of the individual steps of these implementations can be accomplished using a machine learning model trained (as discussed below) to identify appropriate results for that step or by applying a corresponding algorithm. For example, an algorithm can measure an isthmus by determining an isthmus width in various images and tracking the minimal value across the images in different planes. The surgical assistance system 464 can generate implant manufacturing information, or data for generating manufacturing information, based on the computed implant configuration.

In another example, the surgical assistance system 464 can apply the analysis procedure by performing a finite element analysis on a generated three-dimensional model to assess stresses, strains, deformation characteristics (e.g., load deformation characteristics), fracture characteristics (e.g., fracture toughness), fatigue life, etc. The surgical assistance system 464 can generate a three-dimensional mesh to analyze the model. Machine learning techniques to create an optimized mesh based on a dataset of vertebrae, bones, implants, tissue sites, or other devices. After performing the analysis, the results could be used to refine the selection of implants, implant components, implant type, implantation site, etc.

The surgical assistance system 464 performing a finite element analysis on a generated three-dimensional model of implants to assess stresses, strains, deformation characteristics (e.g., load deformation characteristics), fracture characteristics (e.g., fracture toughness), fatigue life, etc. surgical assistance system 464 can generate a three-dimensional mesh to analyze the model of the implant. Based on these results, the configuration of the implant can be varied based on one or more design criteria (e.g., maximum allowable stresses, fatigue life, etc.). Multiple models can be produced and analyzed to compare different types of implants, which can aid in the selection of a particular implant configuration. This analysis technique can be used to select, manufacture, and modify other items, such as delivery instruments (e.g., cannulas, drivers, clamps, etc.), guides (e.g., ports, spreaders, etc.), or the like.

The surgical assistance system 464 can incorporate results from the analysis procedure in suggestions. For example, the results can be used to suggest a surgical plan, select and configure an implant for a procedure, annotate an image with suggested insertions points and angles, generate a virtual reality or augmented reality representation (including the suggested implant configurations), provide warnings or other feedback to surgeons during a procedure, automatically order the necessary implants, generate surgical technique information (e.g., insertion forces/torques, imaging techniques, delivery instrument information, or the like), etc. The suggestions can be specific to implants. In some procedures, the surgical assistance system 464 can also be configured to provide suggestions for conventional implants. In other procedures, the surgical assistance system 464 can be programmed to provide suggestions for patient-specific or customized implants. The suggestion for the conventional implants may be significantly different from suggestions for patient-specific or customized implants.

The system 452 can simulate procedures using a virtual reality system or modeling system. One or more design parameters (e.g., implant configuration, instrument, guides, etc.) can be adjusted based, at least in part, on the simulation. Further simulations can be performed for further refining medical devices. In some embodiments, design changes are made interactively with the simulation and the simulated behavior of the device based on those changes. The design changes can include material properties, dimensions, or the like.

The surgical assistance system 464 can improve efficiency, precision, and/or efficacy of implant surgeries by providing more optimal implant configuration, surgical guidance, customized surgical kits (e.g., on-demand kits), etc. This can reduce operational risks and costs produced by surgical complications, reduce the resources required for preoperative planning efforts, and reduce the need for extensive implant variety to be prepared prior to an implant surgery. The surgical assistance system 464 provides increased precision and efficiency for patients and surgeons.

In orthopedic surgeries, the surgical assistance system 464 can select or recommend implants (e.g., permanent implants, removable implants, etc.), surgical techniques, patient treatment plans, or the like. For example, the implants can be fixation device, joint replacements, hip implants, removable bone screws, stents, or the like. The surgical techniques can be instruments selected based on one or more criteria, such as risk of adverse events, optical implant position, protected zones (e.g., zones with nerve tissue), or the like. In spinal surgeries, the surgical assistance system 464 can select pedicle screw types, dimensions, and/or trajectories to make surgeons more efficient and precise, as compared to existing surgical kits and procedures.

The surgical assistance system 464 can also improve surgical robotics/navigation systems, and provide improved intelligence for selecting implant application parameters. For example, the surgical assistance system 464 empowers surgical robots and navigation systems for spinal surgeries to increase procedure efficiency and reduce surgery duration by providing information on types and sizes, along with expected insertion angles. In addition, hospitals benefit from reduced surgery durations and reduced costs of purchasing, shipping, and storing alternative implant options. Medical imaging and viewing technologies can integrate with the surgical assistance system 464, thereby providing more intelligent and intuitive results.

The surgical assistance system 464 can be incorporated in system 200 (FIG. 2), which can include one or more input devices 420 that provide input to the processor(s) 445 (e.g., CPU(s), GPU(s), HPU(s), etc.), notifying it of actions. The actions can be mediated by a hardware controller that interprets the signals received from the input device and communicates the information to the processors 445 using a communication protocol. Input devices 420 include, for example, a mouse, a keyboard, a touchscreen, an infrared sensor, a touchpad, a wearable input device, a camera- or image-based input device, a microphone, or other user input devices.

Processors 445 can be a single processing unit or multiple processing units in a device or distributed across multiple devices. Processors 445 can be coupled to other hardware devices, for example, with the use of a bus, such as a PCI bus or SCSI bus. The processors 445 can communicate with a hardware controller for devices, such as for a display 430. Display 430 can be used to display text and graphics. In some implementations, display 430 provides graphical and textual visual feedback to a user. In some implementations, display 430 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 440 can also be coupled to the processor, such as a network card, video card, audio card, USB, firewire or other external device, camera, printer, speakers, CD-ROM drive, DVD drive, disk drive, or Blu-Ray device. Other I/O 440 can also include input ports for information from directly connected medical equipment such as MRI machines, X-Ray machines, etc. Other I/O 440 can further include input ports for receiving data from these types of machine from other sources, such as across a network or from previously captured data, for example, stored in a database.

In some implementations, the system 452 also includes a communication device capable of communicating wirelessly or wire-based with a network node. The communication device can communicate with another device or a server through a network using, for example, TCP/IP protocols. System 452 can utilize the communication device to distribute operations across multiple network devices.

The processors 445 can have access to a memory 450 in a device or distributed across multiple devices. Memory 450 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 450 can include program memory 460 that stores programs and software, such as an operating system 462, surgical assistance system 464, and other application programs 466. Memory 450 can also include data memory 470 that can include, e.g., implant surgery information, configuration data, settings, user options or preferences, etc., which can be provided to the program memory 460 or any element of the system 452, such as the manufacturing system 467. The manufacturing system 467 can similar to the system 222 (FIG. 2) and may be include one or more computers, controllers, milling machines, waterjet systems, or other manufacturing equipment.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Areas of interest may be defined in diagnostic data of a patient. In one case, areas of interest based on pre-defined rules or using machine learning models, as described below in relation to FIGS. 9A-13. In another case, the areas of interest may be defined based on a surgeon's input. In one case, the diagnostic data may include images of the patient. The images may be any of camera images, Magnetic Resonance Imaging (MRI) images, ultrasound images, Computerized Aided Tomography (CAT) scan images, Positron Emission Tomography (PET) images, and X-Ray images. In one case, the images of the patients may be stored in a database (e.g., patient surgeon database 310 of FIG. 3).

Figure 5A:
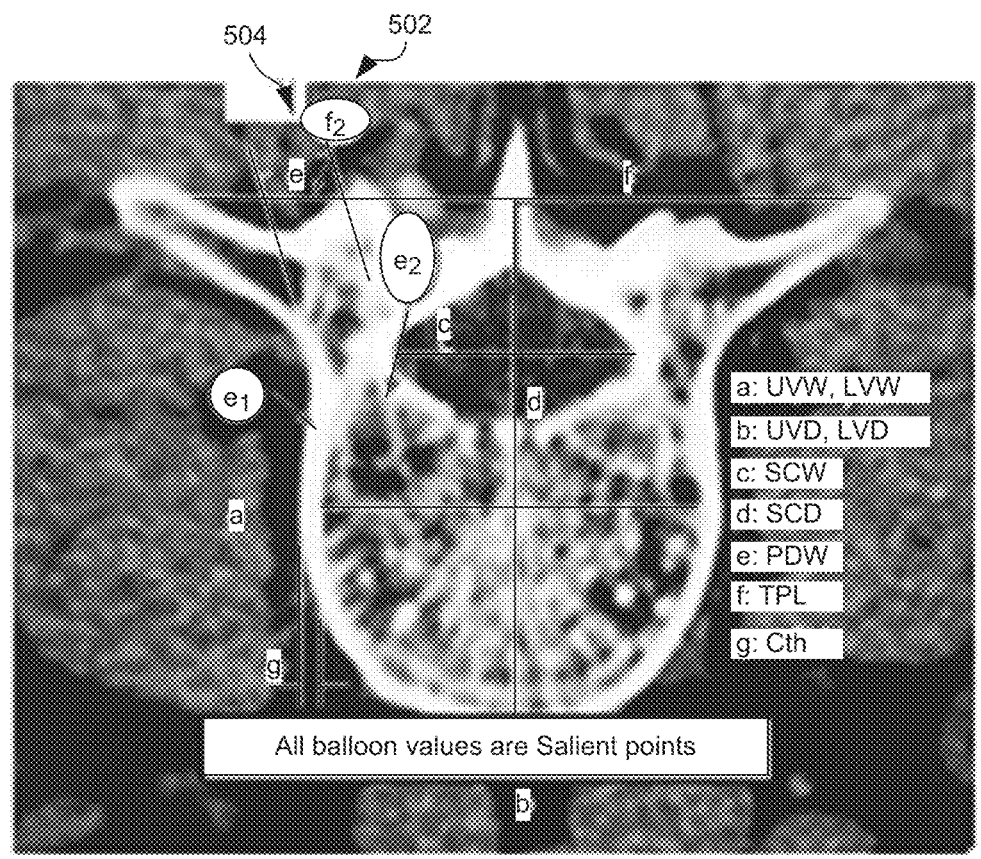
FIG. 5A shows salient points present in a top view of a vertebra of the patient, according to an embodiment.
Figure 5B:
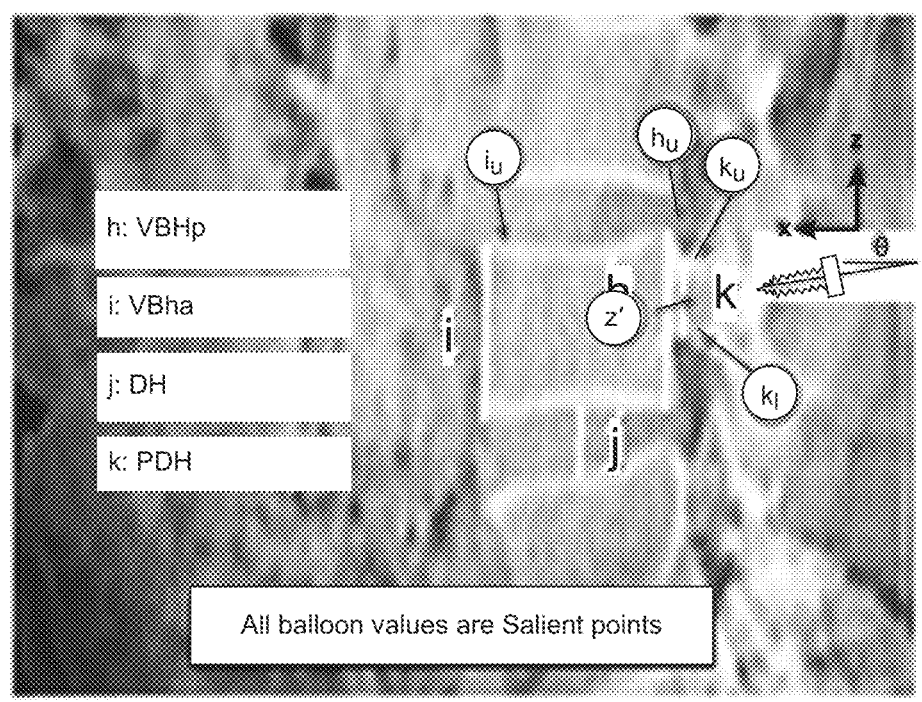
FIG. 5B shows salient points present in a side view of the vertebra of the patient, according to an embodiment.

Post defining the areas of interest, a screw bone type may be defined based on various models and/or the surgeon's input. Successively, salient features of the areas of interest may be identified in the images of the patients, e.g., by applying the procedures described below. FIG. 5A shows salient points present in a top view of a vertebra of the patient. The salient points are shown as bubbles i.e. '$e_1$,' '$e_2$,' and '$f_2$.' Further, FIG. 5B shows salient points present in a side view of the vertebra of the patient. The salient points are shown as bubbles i.e. '$k_l$,' '$k_u$,' '$h_u$,' '$i_u$,' and 'z'.

Figure 6A:
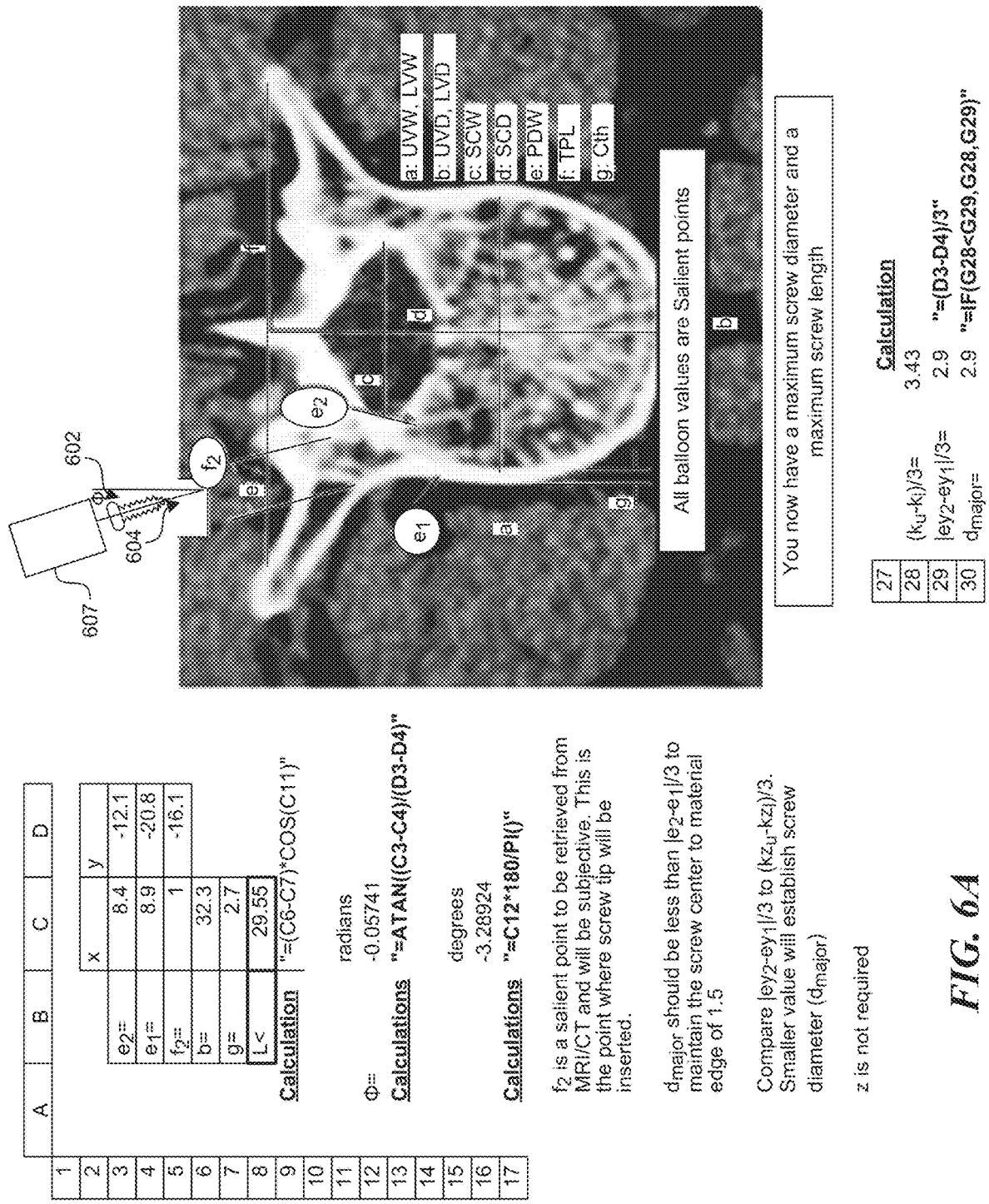
FIG. 6A illustrates computations for determining an XZ angle ($\phi$), according to an embodiment.

Successively, based on the salient points of the areas of interest, the system 202 or 452 may determine implant information (e.g., angles and position entry point for implant orientation, implant insertion, and implant movement, etc.). FIG. 6A illustrates computations for determining the XZ angle ($\phi$) 602 using the salient points. It should be noted that positions of X and Y co-ordinates of the regions of interest may be determined based on a location of at least one salient feature present in the image.

Figure 6B:
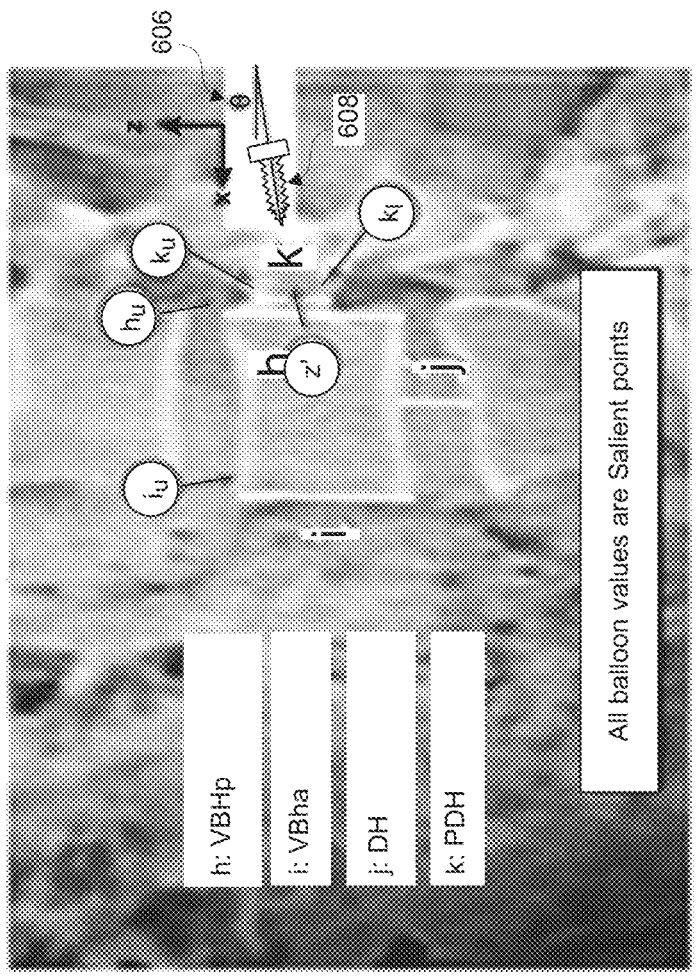
FIG. 6B illustrates computations for determining an XY angle ($\theta$), according to an embodiment.

FIG. 6B illustrates computations for determining the XY angle (θ) 606 using the salient points. It should be noted that positions of X and Y co-ordinates of the regions of interest may be determined based on a location of at least one salient feature present in the image. Further, FIG. 6A illustrates a position entry point 604 for the guide 607 and spinal screw and FIG. 6B illustrates a position entry point 608 for the spinal screw. Upon determining, a procedure MRI data including the XY angle, the XZ angle, and the position entry point for the spinal screw, may be stored in the abnormalities module.

Post identification of the angels and the entry point for an implant, the system 202 or 452 may determine additional implant configuration features. For example, the system 202 or 452 can determine a maximum implant (e.g., spinal screw) diameter, a minimum implant diameter, and a length of the implant to be used during a spinal surgery. For example, upon determining the maximum spinal screw diameter and the length of the spinal screw, the procedure MRI data may be updated in the abnormalities module.

Figure 7:
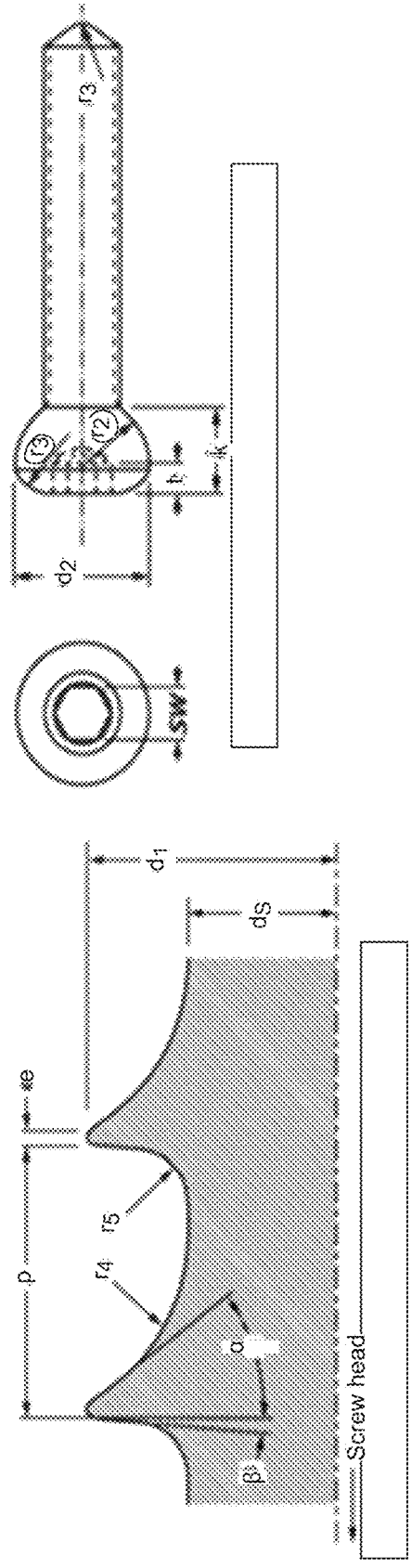
FIG. 7 illustrates a spinal screw HA and dimensions of the spinal screw HA, according to an embodiment.

In the spinal surgery example, the spinal screw having determined maximum screw diameter and the length may be identified. The spinal screw may be suggested, to the surgeon, for usage during the spinal surgery. In one case, a spinal screw HA and dimensions of the spinal screw HA may be illustrated for the surgeon's selection, as shown in FIG. 7. FIG. 7 illustrates a schematic showing different parameters of the spinal screw HA, dimensions of the spinal screw HA, and a schematic of threads of the spinal screw HA. Further, different such details related to spinal screws HB, spinal screw HD, and other known spinal screws may be presented to the surgeon for usage during the spinal surgery.

Figure 8A:
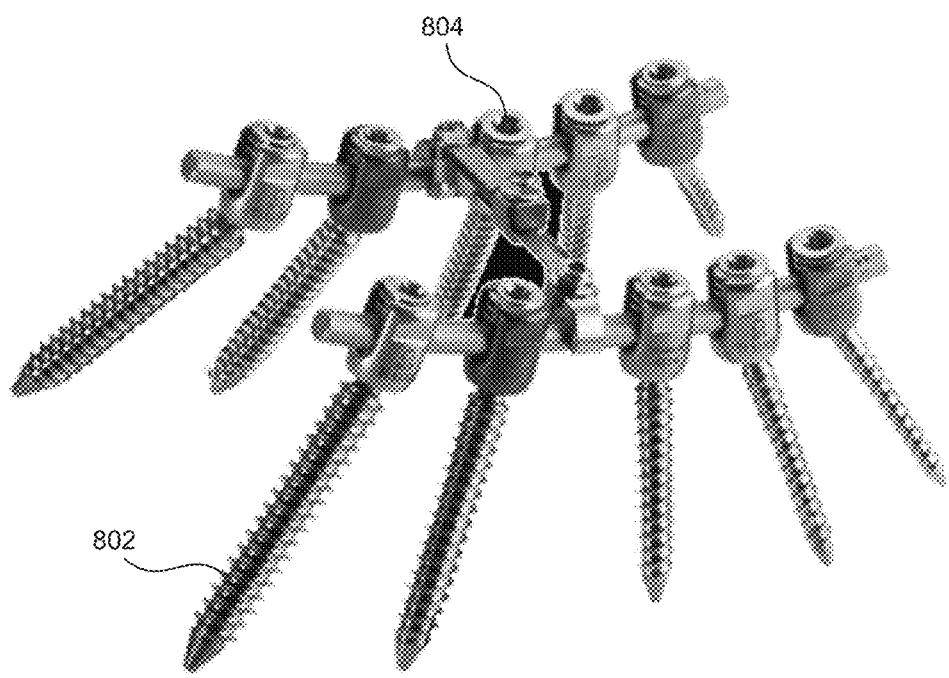
FIG. 8A illustrates a Three Dimensional (3D) printed set of screw shapes and a screw guide, according to an embodiment.
Figure 8B:
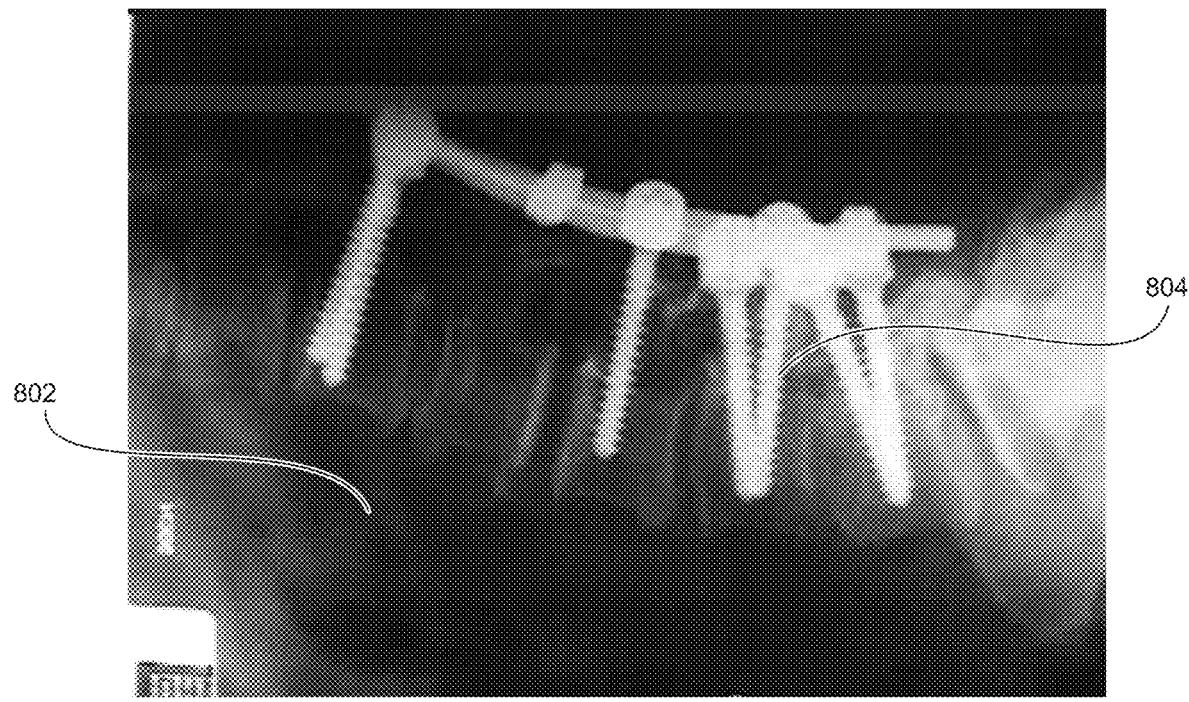
FIG. 8B illustrates an X-ray image of a spine of a patient with a 3D printed set of spinal screws and a screw guide surgically inserted into the spine of a patient, according to an embodiment.

FIG. 8A illustrates a three dimensional (3D) printed set of screw shapes and a screw guide, according to an embodiment. FIG. 8B illustrates an X-ray image of a spine of a patient with a 3D printed set of spinal screws and a screw guide surgically inserted into the spine of a patient, according to an embodiment. The screws shapes can be designed based on the details and parameters discussed in connection with FIG. 7.

Different parts of a patient's body can be analyzed. Salient points can be selected based on the implantation site and can be reference features, points along delivery paths, points at the implantation site, or the like. As one example, for an ACL replacement, upon determining the entry point and angle for a tibial tunnel for attaching a replacement graft, the system 200 or 452 can identify a depth for the tibial tunnel such that it will end above the center of the knee joint without piercing surrounding tissue. In addition, dimensions for the ACL graft itself and/or for screws or other fastening components can be suggested.

Figure 9:
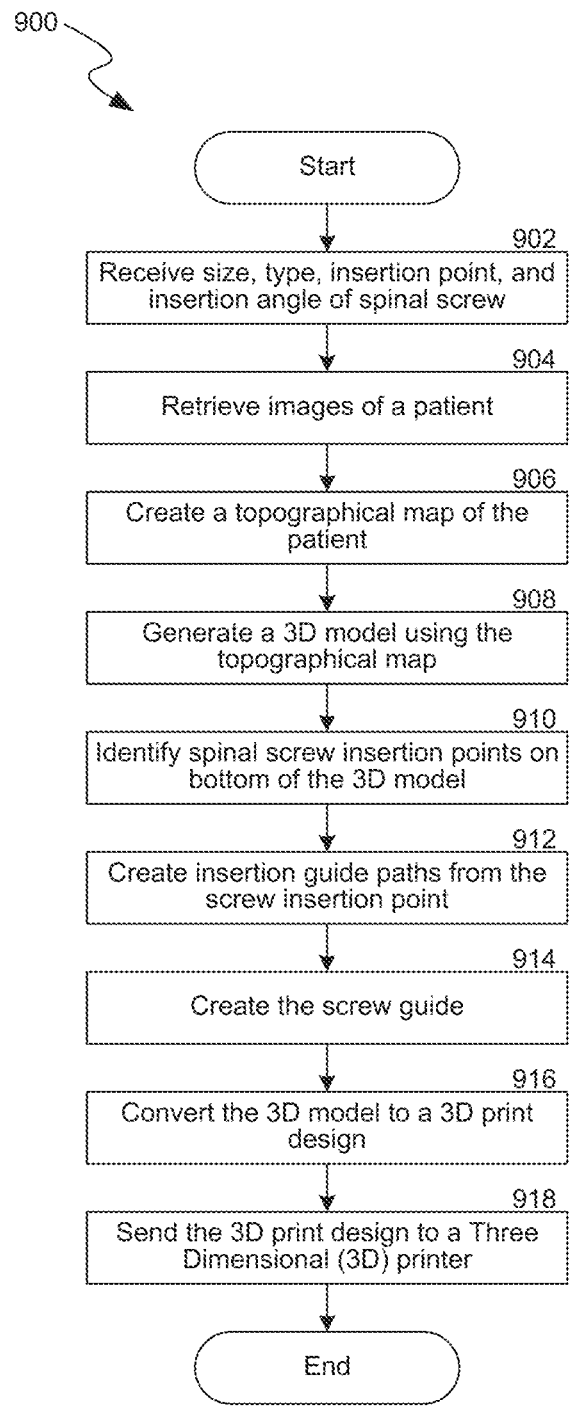
FIG. 9 illustrates a flowchart showing a method executed by a guide design module of the system, according to an embodiment.

Functioning of guide design modules (e.g., guide design module 218 of FIG. 2) will now be explained with reference to a flowchart 900 shown in FIG. 9, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

At first, details related to a spinal screw may be received, at step 902. The details may be received from the PSNB module 208 (FIG. 2). The details may include a size, type, insertion point, and an insertion angle of the spinal screw.

Post receiving details related to the spinal screw, images of a patient may be retrieved, at step 904. The images may be retrieved from the PSNB module 208. In one case, the images may be any of camera images, Magnetic Resonance Imaging (MRI) images, ultrasound images, Computerized Aided Tomography (CAT) scan images, Positron Emission Tomography (PET) images, and X-Ray images. The images may be analyzed to identify anomalies present in a spine of the patient. Further, preliminary information regarding locations of screw placement during a spinal surgery may also be determined based on analysis of the images.

Post receiving the images, a topographical map of the patient may be created, at step 906. The topographical map may be created based on processing of the images using train mapping algorithms. The topographical map may include a map of the patient's body on which the screw guide needs to be placed. In an embodiment, if the screw guide is to be placed on the patient's back, the topographical map may include a map of the patient's back. The topographical map may include all the curves, contours and terrain of the patient's back.

In another embodiment, the spinal operation may be performed through an abdomen of the patient. During such case, a bottom part of the screw guide may be mapped with the contours of the abdomen of the patient. In such a case, the topographical map may be created in congruence with the patient's abdomen.

Post generating the topographical map of the patient, a Three-Dimensional (3D) model is generated using the topographical map of the patient, at step 908. Further, the topographical map of the patient may be generated on the bottom of the 3D model. A patient facing surface of the screw guide may be designed based on the topography map. In one case, a surface opposite to the patient facing surface may be at least one inch away from a highest point of the patient facing surface. These two surfaces may be used to create the 3D model of the screw guide. Other types of models or virtual representations can be generated.

Successively, screw insertion points may be identified on bottom of the 3D model, at step 910.

Successively, insertion guide paths may be created from the screw insertion point, at step 912. Specifically, the insertion guide paths may be created using the screw insertion point to top of the 3D model.

Thereafter, the screw guide may be created, at step 914. The screw guide may be created using a top portion and a bottom portion of the 3D model. Successively, screw insertion points may be identified on the screw guide. Openings large enough to accommodate the spinal screw, but narrow enough to ensure desired location and angle may be added to the 3D model of the screw guide.

The 3D model may be converted into a 3D print design, at step 916. In an embodiment, software may convert the 3D model to the 3D print design.

Successively, the 3D print design may be sent to a 3D printer, at step 918. The spinal screw and the screw guide may be printed using a Three-Dimensional (3D) printer 222. The 3D printer 222 may be any general purpose 3D printer utilizing technologies such as Stereolithography (SLA), Digital Light Processing (DLP), Fused Deposition Modeling (FDM), Selective Laser Sintering (SLS), Selective laser melting (SLM), Electronic Beam Melting (EBM), Laminated object manufacturing (LOM) or the like.

The method 900 can be used to perform other types of procedures. To use a catheter, a model representation of the area of interest can be generated using the map at step 908. At step 910, a catheter can be identified and modified based on the model representation. At step 912, insertion points, delivery paths, and other information can be generated from the model representation. At step 914, delivery instruments, and other tools can be produced based on patient information. At step 916, the model or representation can be used to generate manufacturing data, such as 3D printing data. At step 918, the manufacturing data can be sent to a manufacturing device that produces technology, such as a distal portion of the catheter. Accordingly, the method 900 can be used to produce a wide range of surgical instruments and tools customized for the patient.

Objectives and criteria can be used at various points in the method 900 to provide further customization. The manufacturing equipment can be located at a hospital to allow surgical kits or components thereof to be manufactured during the surgical session. This allows on-demand fabrication of tools and instruments in real time during a surgical procedure. If a surgeon encounters unexpected events during surgery, additional tools or implants can be manufactured.

Figure 10:
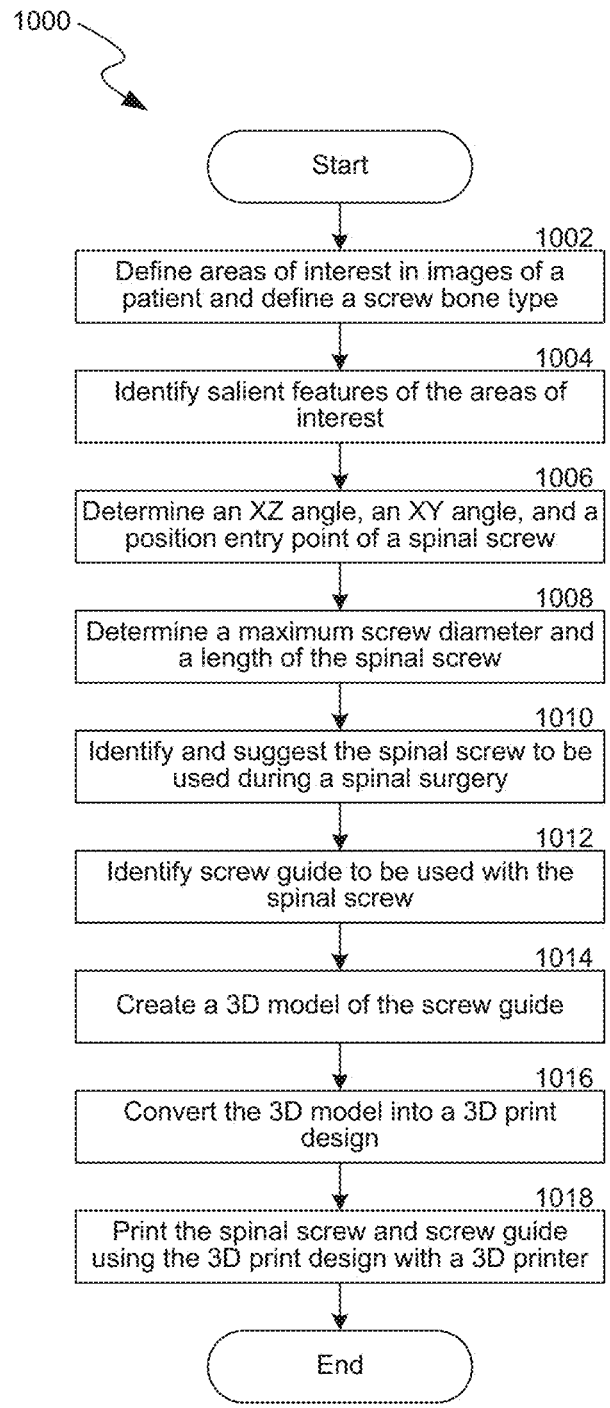
FIG. 10 illustrates a flowchart showing a method for assisting a surgeon in screw placement during a spinal surgery, according to an embodiment.

The flowchart 1000 of FIG. 10 shows the architecture, functionality, and operation for assisting a surgeon in screw placement during a spinal surgery, according to an embodiment. In this regard, each block may represent a module, segment, or portion of code, which comprises one or more executable instructions for implementing the specified logical function(s). It should also be noted that in some alternative implementations, the functions noted in the blocks may occur out of the order noted in the drawings. For example, two blocks shown in succession in FIG. 10 may in fact be executed substantially concurrently or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine. The flowchart 1000 starts at step 1002 and proceeds to step 1018.

At step 1002, areas of interest may be defined in diagnostic data of a patient and a screw bone type may be defined, during a spinal surgery. The diagnostic data may comprise images of the patient. The images may be any of camera images, Magnetic Resonance Imaging (MRI) images, ultrasound images, Computerized Aided Tomography (CAT) scan images, Positron Emission Tomography (PET) images, and X-Ray images.

At step 1004, salient features of areas of interest may be identified from the diagnostic data. In one case, the images may be analyzed to identify abnormalities and the salient features, for performing spinal surgeries on the patients.

At step 1006, an XZ angle, an XY angle, and a position entry point for a spinal screw are determined. In one case, the XZ angle, the XY angle, and the position entry point may be determined based on the salient features.

At step 1008, a maximum screw diameter and a length of the spinal screw to be used during the spinal surgery may be determined based on the XY angle, the XZ angle, and the position entry point of the spinal screw. Upon determining the maximum screw diameter and the length of the spinal screw, the procedure MRI data may be updated in an abnormalities module 210 (FIG. 2).

At step 1010, the screw implant to be used during a spinal surgery may be identified and suggested to a surgeon. The screw implant may be identified based on the maximum screw diameter and the length of the spinal screw.

At step 1012, a screw guide to be used with the spinal screw may be identified. The screw guide may be identified based on the maximum screw diameter and the length of the spinal screw.

At step 1014, a 3D model of the screw guide is generated to be used during the spinal surgery.

At step 1016, the 3D model is converted into a 3D print design to be used during the spinal surgery.

At step 1018, the 3D print design may be used to print the spinal screw and the screw guide, using a 3D printer.

Figure 11:
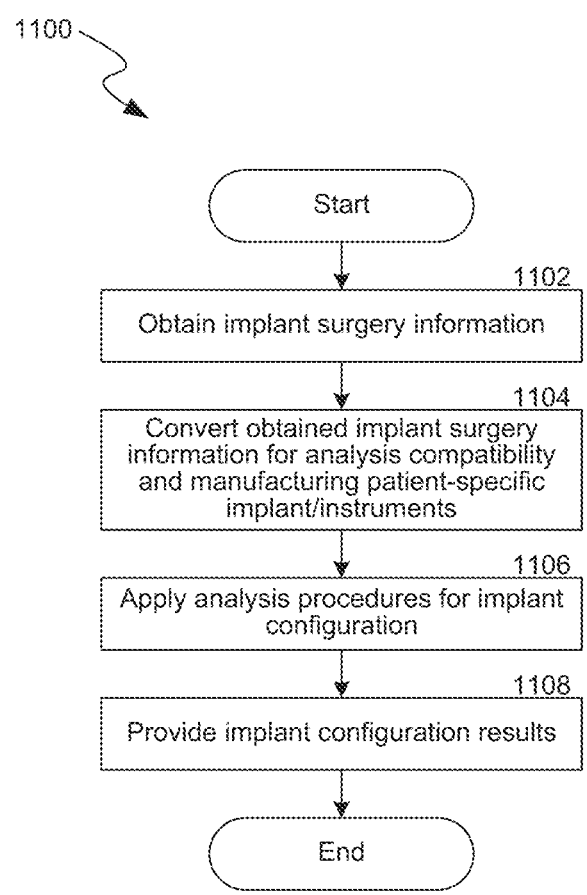
FIG. 11 illustrates a flowchart showing a method for generating implant configurations.

FIG. 11 illustrates a flowchart showing a method 1100 for generating implant configurations. At block 1102, method 1100 can obtain implant surgery information such as images, patient history, circumstance, test results, biographic data, surgeon recommendations, implant specifics, etc. Implant surgery images can be of parts of a patient, such as camera images, Magnetic Resonance Imaging (MRI) images, ultrasound images, Computerized Aided Tomography (CAT) scan images, Positron Emission Tomography (PET) images, X-Ray images, 2D or 3D virtual models, CAD models, etc. Additional implant surgery information can include, e.g., sex, age, height, weight, type of pathology, occupation, activity level, implant types and dimensions, availability of available implants, or aspects of a surgeon's preoperative plan (e.g., surgeon's initial implant configuration, detection and measurement of the patient's anatomy on images, etc.).

The implant surgery information can be obtained in various manners such as through direct user input (e.g., through a terminal or by interacting with a web service), through automatic interfacing with networked databases (e.g., connecting to patient records stored by a hospital, laboratory, medical data repositories, etc.), by scanning documents, or through connected scanning, imaging, or other equipment. The patient data can be gathered with appropriate consent and safeguards to remain HIPPA compliant.

At block 1104, method 1100 can convert the implant surgery information obtained at block 1102 to be compatible with analysis procedures. The conversion can depend on the analysis procedure that will be used. As discussed below in relation to block 1106, analysis procedures can include directly applying a machine learning model, applying an algorithm with multiple stages where any of the stages can provide machine learning model predictions (see FIG. 12A), or applying a virtual modeling system (see FIG. 12B).

In some implementations, the conversion of the implant surgery information can include formatting the implant surgery information for entry to a machine learning model. For example, information such as patient sex, height, weight, etc. can be entered in a feature vector, such as a sparse vector with values corresponding to available patient characteristics. In some implementations, the conversions can include transforming images from the implant surgery information into a format suitable for input to a machine learning model, e.g., an array of integers representing pixels of the image, histograms, etc. In some implementations, the conversion can include identifying surgery target features (detection and measurement of the patient's anatomy on images), characterizing surgery targets, or modeling (i.e. creating a virtual model of) the implant surgery target. For example, in a spinal surgery, this can include measuring vertebrae features on an image, converting 2D images of vertebrae into a 3D model, or identifying which vertebrae from a series of images are to be the target of the implant operation. As another example, in an ACL replacement surgery, this can include identifying and measuring features in an image such as location, size, and spacing of anatomy such as of the femur, patella, remaining portion of meniscus, other ligaments, etc., converting 2D images of the knee into a 3D model, or identifying other areas of damage (e.g., fractures, torn cartilage, other ligament tears, etc.).

In various implementations, the conversion process can be automatic, human supervised, or performed by a human technician, e.g., using tools such as a digital ruler and a digital angle finder. Further in the spinal surgery example, the conversion can include identifying a target set of vertebrae, initially localizing and marking the target set of vertebrae, performing segmentation for each of the target set of vertebrae, and marking cortical boundaries. In some implementations, input for the spinal implant surgery can specify a target set of vertebrae, however the surgical assistance system can automatically perform calculations for additional vertebrae that weren't specified in the inputs. This can give the surgeon an option to expand the set of vertebrae to be fused, either prior to the operation or even during the procedure. In the ACL replacement surgery example, the conversion can include identifying a graft type (e.g., patella tendon, hamstring, cadaver ACL, etc.), initially localizing or marking the target drilling sites, performing segmentation for the target features (e.g., end of the femur), and marking boundaries (e.g., bone edges, meniscus edges, synovial membrane, etc.).

At block 1106, method 1100 can apply analysis procedures, using the converted implant surgery information from block 1104, to identify implant configuration(s). In various implementations, the analysis procedures can include directly applying a machine learning model, applying a sequence of steps that can include one or more machine learning models, and/or generating a virtual model of the surgery target area and applying heuristics for implant configuration selection.

To apply a machine learning model directly, method 1100 can provide the converted implant information to a machine learning model trained to specify implant configurations. A machine learning model can be trained to take input such as representations of a series of images and a feature vector for the patient and other aspects of the surgery (e.g., implant availability, surgeon specialties or ability indicators, equipment available, etc.) and can produce results that implant configurations. For example, for a spinal surgery, the machine learning model can suggest pedicle screw configurations, e.g., characteristics such as screw diameter, length, threading and application parameters such as screw insertion point, angle, rotation speed, etc. As another example, for an ACL replacement surgery, the machine learning model can suggest graft type, attachment type (e.g., screw material, length, or configuration features), graft attachment locations, drill depths, etc.

In some implementations, the converted implant information can be used in a multi-stage process for selecting aspects of an implant configuration. For example, for a spinal surgery, the multi-stage process can include method 900 or method 1000, discussed below. In various steps of this these processes, either an algorithm can be used to generate results for that step or a machine learning model, trained for that step, can be applied.

In some implementations, the procedure for identifying implant configurations for a spinal surgery can include processing implant surgery information to locate targeted vertebrae and their pedicles in images, on available axes; identifying and tagging vertebrae characteristics; determining a preferred screw insertion point based on a mapping between tags and insertion point criteria (e.g., where the mapping can be a representation of a medical definition of a pedicle screw insertion point—described below); performing measurements, on the images, of the pedicle isthmus width and height and length of the pedicle and vertebral body, starting at the preferred insertion point; measuring the angle between the line used to determine length and the sagittal plane, in the axial view; and measuring the angle between that length line and the axial plane.

In some implementations, machine learning models can be trained to perform some of these tasks for identifying implant configurations. For example, machine learning models can be trained to identify particular vertebral pedicles in various images, which can then be atomically measured and aggregated across images, e.g., storing minimal, maximal, median, or average values, as appropriate given the target being measured. As another example, a machine learning model can receive the set of images and determine an order or can select a subset of the images, for automatic or manual processing. In some implementations, a machine learning model can be used to localize and classify the target within an image, such as by identifying a target vertebra or localizing the end of the femur or meniscus edges. In some implementations, a machine learning model can be used to segment target vertebrae, femur, tibia, or other anatomical features in the target area, to determine their boundaries. In some implementations, a machine learning model can be used to localize insertion points. In some implementations, a machine learning model can be used to segment images to determine boundaries of anatomical structures (e.g., boundaries of bones, organs, vessels, etc.), density of tissue, characteristics of tissue, or the like.

In various implementations, the results from the above stages can be used in inference formulae to compute the implant configurations. For example, a maximal screw diameter can be determined using the smallest pedicle isthmus dimension found across all the images of the target vertebrae (which can be adjusted to include a safety buffer). As another example, a maximal screw length can be determined using the smallest measurement of pedicle and vertebral body length, across all the target vertebra in question (which can be adjusted to include a safety buffer).

Machine learning models, as used herein, can be of various types, such as Convolutional Neural Networks (CNNs), other types of neural networks (e.g., fully connected), decision trees, forests of classification trees, Support Vector Machines, etc. Machine learning models can be trained to produce particular types of results, as discussed below in relation to FIG. 13. For example, a training procedure can include obtaining suitable training items with input associated with a result, applying each training item to the model, and updating model parameters based on comparison of model result to training item result.

In some implementations, automated selection of implant configurations can be limited to only cases likely to produce good results, e.g., only for certain pathologies, types of patients, surgery targets (e.g., the part of the spine that needs to be fused), or where confidence scores associated with machine learning model outputs are above a threshold. For example, in the spinal surgery example, automation can be limited to common types of spinal fusions, such as L3/L4, L4/L5, or L5/S1, certain pathologies such as spondylolisthesis or trauma, or patients with certain characteristics, such as being in a certain age group. As another example, for an ACL replacement, automation can be limited to cases without other ligament tears.

At block 1108 of FIG. 11, method 1100 can provide results specifying one or more features of an implant configuration. For example, the results for a spinal surgery can include selection of pedicle screw type and dimensions for each vertebra and guidance on an insertion point and angle for each screw. As another example, results for an ACL replacement surgery can include selection of implant graft type, connection type, joint dimensions, and guidance on connection points such as drill locations and depths. In some implementations, the results can be specified in a natural language, e.g., using templates that can be filled in with recommendations. In some cases, the results from the analysis of block 1106 can be mapped to particular reasons for the implant configuration recommendations, and these reasons can be supplied along with the recommendations.

In some implementations, the results can be based on medical definitions of preferred implant configurations, where the preferred implant configurations can be mapped to a particular surgical target area based on the results from block 1106. For example, results for spinal surgery pedicle screws can include a preferred insertion point, e.g., defined, for lumbar vertebrae, at the intersection of the superior articular facet, transverse process, and pars interarticularis; and for thoracic spine or cervical spine, at the intersection of the superior articular facet plane and transverse process. As another example, a preferred screw angle can be, in axial view, the angle between the sagittal plane and the line defined by the insertion point and midpoint of the pedicle isthmus. In sagittal view the preferred screw angle can be parallel to the superior vertebral endplate. In addition, a maximal screw length can be defined as the distance between the insertion point and the far cortical boundary of the vertebra, at a particular screw angle. A maximal screw diameter can be the minimal width of the pedicle isthmus, on any axis. Each of these can be modified to include a certain safety buffer, which can vary depending on the size of the vertebra. The results from block 1106 can identify features of an individual patient, which can be used in conjunction with the foregoing implant configuration definitions to specify patient-specific implant configurations, e.g., in natural language, as image annotations, in a 3D model, as discussed below.

The implant configuration results can be specified in various formats. For example, results can be in a natural language, coordinates one of various coordinate systems, as instructions for a robotic system, as annotations to one or more images, or as a virtual model of the surgery target area. The results can be used to augment the implant surgery in multiple ways. For example, results can be added to a preoperative plan. Results can trigger acquisition of implant materials, such as by having selected implants ordered automatically or having designs for patient-specific screws provided for 3D-printing. As another example, results can be used to provide recommendations during a surgical procedure, e.g., with text or visual annotations provided as overlies on a flat panel display, through auditory or haptic feedback alerts, or using an AR or VR system, e.g., to display an overlay of the implant on the patient anatomy or to display guidance on the suggested insertion point and angle. In some implementations, the results can be used to control robotic systems, e.g., causing a robotic arm to align itself according to the recommended insertion point and angle, which may be first confirmed by a surgeon.

The method 1100 can be used in a wide range of procedures, e.g., open procedures, minimally invasive procedures, orthopedic procedures, neurological procedures, reconstructive implants, maxillofacial procedures (e.g., maxillary implants), or other procedure. In some surgical procedures, the implant information at block 1102 can include implant dimensions, material information (e.g., composition of implant), and images of the patient. At block 1106, the implant configuration can be implant dimensions (e.g., when in a delivery state or implanted state), implant functionality, or the like.

Figure 12A:
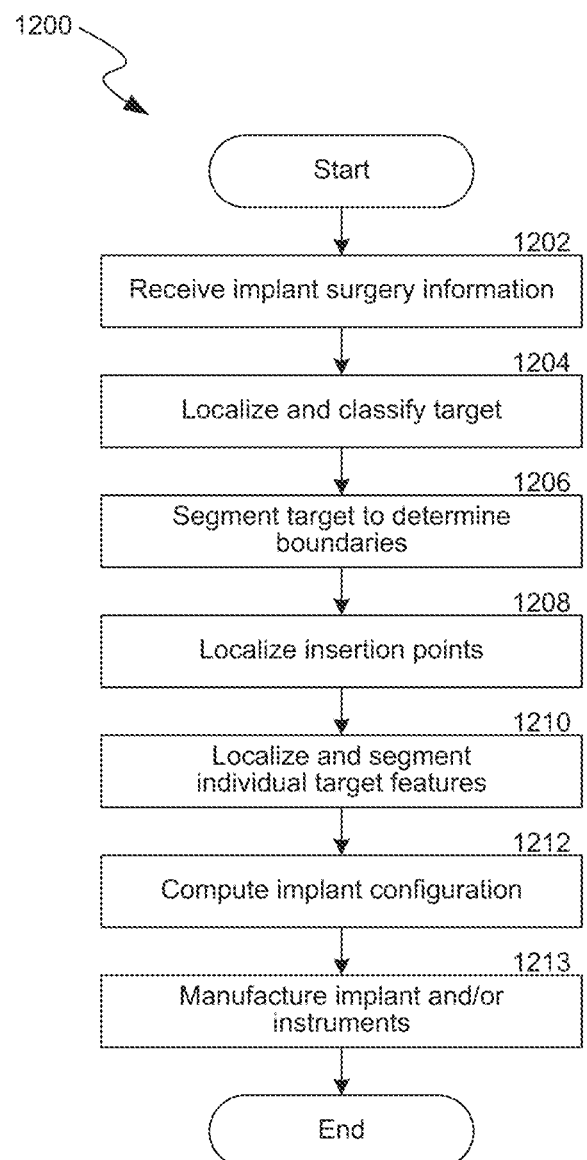
FIG. 12A illustrates a flowchart showing a method for applying analysis procedures that can utilize machine learning models, according to an embodiment.

FIG. 12A illustrates a flowchart showing a method 1200 for applying analysis procedures that can utilize machine learning models, according to an embodiment. In some implementations, method 1200 is performed as a sub-process of block 1106 (FIG. 11). At block 1202, method 1200 can receive implant surgery information. This can be some of the converted implant surgery information from block 1204. In some implementations, the implant surgery information can include one or more images of the surgery target area, e.g., MRI scans of a spine, X-rays of a wrist, ultrasound images of an abdomen, etc.

At block 1204, method 1200 can localize and classify a target in one or more of the images of the surgery target area. In various implementations, this can be accomplished by applying a machine learning model trained for the particular target area to identify surgical targets or by finding a centroid point of each displayed vertebra, performing vertebral classification using image recognition algorithms, and determining whether the classified vertebrae match a list of vertebrae identified for the surgery. In some implementations, if the image does not contain at least one target of interest, the image can be disregarded from further processing.

At block 1206, method 1200 can segment the identified target(s) from block 1204 to determine their boundaries. At block 1208, method 1200 can localize implant insertion points. In some implementations, blocks 1206 and 1208 can be performed using machine learning models or algorithms, e.g., that identify particular patterns, changes in color, shapes, etc.

At block 1210, method 1200 can localize and segment individual target features. For example, in a spinal surgery where targets are vertebrae, at block 1210 method 1200 can identify vertebrae pedicles and their isthmus, and measure these features. In some implementations, this can be accomplished using a machine learning model trained to detect each type of feature. In some implementations, detecting the pedicle and the isthmus of vertebra from annotated images can include measuring the isthmus width and tracking the minimal value across images and planes, defining the angle between the line that passes through at least two midpoints in the pedicle, and the reference plane, measuring the maximal length through that line, and tracking the minimal value across measurements. In some implementations, isthmus determination and measurement can be accomplished by starting at a point inside a pedicle, computing the distance to pedicle borders in multiple directions, taking the minimum length. In other implementations, the isthmus determination and measurement can be accomplished by scanning, for example using horizontal lines that intersect with pedicle borders in an axial view, and finding the minimum-length line.

In some implementations, the steps performed at any of blocks 1204-1210 can be repeated for each of multiple target area images, aggregating results from the multiple images. For example, in a step for identifying and measuring vertebrae pedicles, an aggregated measurement for a particular pedicle can be the minimum measured width of the pedicle from all of the images showing that particular pedicle.

At block 1212, method 1200 can use results from any of blocks 1204-1210 to compute an implant configuration (e.g., characteristics and application parameters). For example, the minimum width of a pedicle found across the images showing that pedicle, with some buffer added, can be the selected width characteristic of a pedicle screw implant. As another example, a screw angle could be determined using an identified insertion point and a center of the pedicle isthmus, with respect to center axis, depending on the image plane. The angles in axial and sagittal planes can be either the median or average angles across the multiple images. As a further example, a maximal screw length can be determined as the length of the line defined by the insertion point, the insertion angle, and the point where the line hits the cortical wall of the vertebra, minus some safety buffer. This length can be computed from multiple images and the minimum across all the images can be used for of this screw.

At block 1213, method 1200 can include manufacturing medical devices, such as implants, instruments, or the like. The results from block 1212 can be used to produce the devices.

Figure 12B:
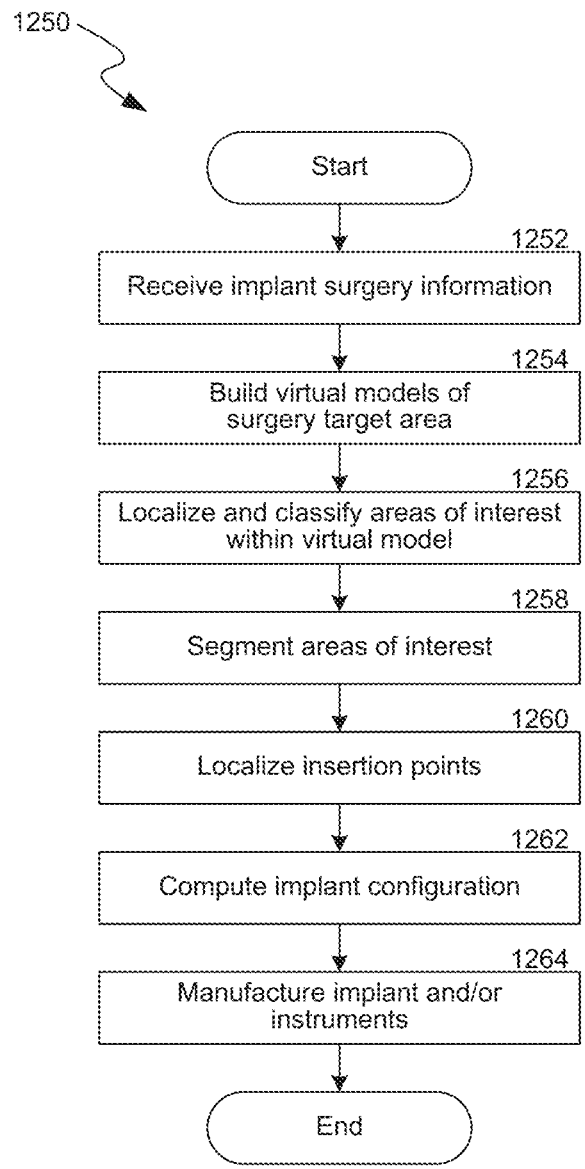
FIG. 12B illustrates a flowchart showing a method for applying analysis procedures that can utilize virtual models, according to an embodiment.

FIG. 12B illustrates a flowchart showing a method 1250 for applying analysis procedures that can utilize virtual models, according to an embodiment. In some implementations, method 1250 is performed as a sub-process of block 1256. At block 1252, method 1250 can receive implant surgery information. This can be some of the converted implant surgery information from block 1104 (FIG. 11). In some implementations, the implant surgery information can include one or more images of the surgery target area.

At block 1254, method 1250 can build one or more virtual models of the target surgery area based on the images and/or other measurement data in the implant surgery information. A virtual model, as used herein, is a computerized representation of physical objects, such as the target area of a surgery (e.g., portions of a patient's spine) and/or implants (e.g., screws, rods, etc.). In some implementations, virtual models can be operated according to known physical properties, e.g., reactions to forces can be predicted according to known causal relationships. In various implementations, the virtual models generated by method 1250 can be two-dimensional models or three-dimensional models. For example, a two-dimensional model can be generated by identifying portions of an image as corresponding to parts of a patient's anatomy, such that a computing system can determine how implant characteristics would fit in relation to the determined anatomy parts. As another example, a three-dimensional model can be generated by identifying shapes and features in individual images, from a set of successive images, and mapping the identified shapes and features into a virtual three-dimensional space, using relationships between images. Finite element analysis techniques can be used to predict stresses, strains, pressures, facture, and other information and can be used to design implants, surgical tools, surgical techniques, etc. For example, the implant configuration can be determined based on predetermined stresses (e.g., maximum allowable stresses in the tissue and/or implant, yield strength of anatomical structures and/or implant components, etc.), fracture mechanics, or other criteria defined by the physician or automatically determined based on, for example, tissue characteristics, implant design, or the like. In some embodiments, fatigue life can be predicted using stress or strain based techniques.

A virtual model can also analyze mechanical interaction between a patient's vertebrae, loading of implants, and other devices (e.g., rods, ties, brackets, plates, etc.) coupled to those implants. The output of these analyses can be used to select pedicle screw configurations, insertion trajectories, and placement location to optimize screw pull-out strength, maximum allowable loading (e.g., axial loads, shear loads, moments, etc.) to manage stresses between adjacent vertebrae, or maximum allowable stress in regions of the bone at risk for fracture.

In some embodiments, a user could identify areas of weakened bone or areas on images of the patient where there is risk of a fracture due to the presence of a screw or other implant. This information can be provided to the virtual model. The virtual model can be used to evaluate whether the configuration or location of the implant would create an unacceptable risk of fracture in the identified region. If so, the system could alert the user to that risk or modify the implant configuration or the procedure to reduce the risk to an acceptable level. In other embodiments, the system could identify these areas of high fracture risk automatically. In yet another embodiment, the system could provide data to the user such as the maximum torque to apply to a given pedicle screw during the surgical procedure such that tissue trauma, risk of fracture, or adverse advents is minimized.

At block 1256, method 1250 can localize and classify areas of interest within the virtual model(s) from block 1254. This can be accomplished using object recognition that matches shapes of known objects to shapes within the virtual models. For example, in a virtual model for a spinal surgery, the images can be MRI images of vertebrae. The virtual vertebrae can be labeled (e.g., c1-s5) and virtual model vertebrae corresponding to the vertebrae for which the spinal procedure is planned can be selected as the areas of interest. In some implementations, additional areas around the selected areas can be added to the areas of interest, allowing the surgeon to select alternative options before or during the procedure. For example, the one or two vertebrae adjacent, on one or both sides, to the planned vertebrae can be additionally selected.

At block 1258, method 1250 can segment the areas of interest, identified at block 1256, to determine various boundaries and other features, such as the pedicle boundaries and the pedicle isthmus. In some implementations, the segmentation or boundary determinations can be performed using a machine learning model. The machine learning model can be trained, for the type of implant surgery to be performed, to receive a portion of a virtual model and identify target portion segmentations or boundaries.

At block 1260, method 1250 can localize an insertion point for the implant in the target area. In some implementations, this can be accomplished by applying a machine learning model trained to identify insertion points. In some implementations, localizing insertion points can be accomplish using an algorithm, e.g., that identify particular patterns, changes in color, shapes, etc. identified as corresponding to preferred implant insertion points.

At block 1262, method 1250 can compute an implant configuration based on the virtual model(s) and/or determinations made in blocks 1256-1260. In some implementations, the implant can be associated with requirements for their application and properties to maximize or minimize. In these cases, the implant configuration can be specified as the configuration that fits with the virtual model, achieving all the requirements, and optimizing the maximizable or minimizable properties. For example, when method 1250 is performed to determine pedicle screw configurations for a spinal surgery, virtual pedicle screws can be placed in a virtual model generated at block 1254, according to the insertion points determined at block 1260. The virtual pedicle screws can further be placed to: not breach cortical vertebral boundaries (e.g., determined at block 1258), with a specified amount of buffer, while maximizing the screw diameter and length, taking into consideration required buffers and close to optimal insertion angle, defined by the pedicle isthmus center and insertion point, for each vertebra (e.g., determined at block 1258). In some implementations, this placement of the implant can be performed as a constraint optimization problem. For example, a virtual screw can be placed inside the segmented vertebral body in the virtual model. The placement can then be adjusted until an equilibrium is reached that optimizes the parameters while conforming to the implant constraints. For example, method 1250 can maximize screw diameter and length while aligning with an optimal angle and avoiding cortical breaches.

At block 1264, method 1250 can include manufacturing medical devices, such as implants, instruments, or the like. The results from block 1262 can be used to produce the devices.

Figure 13:
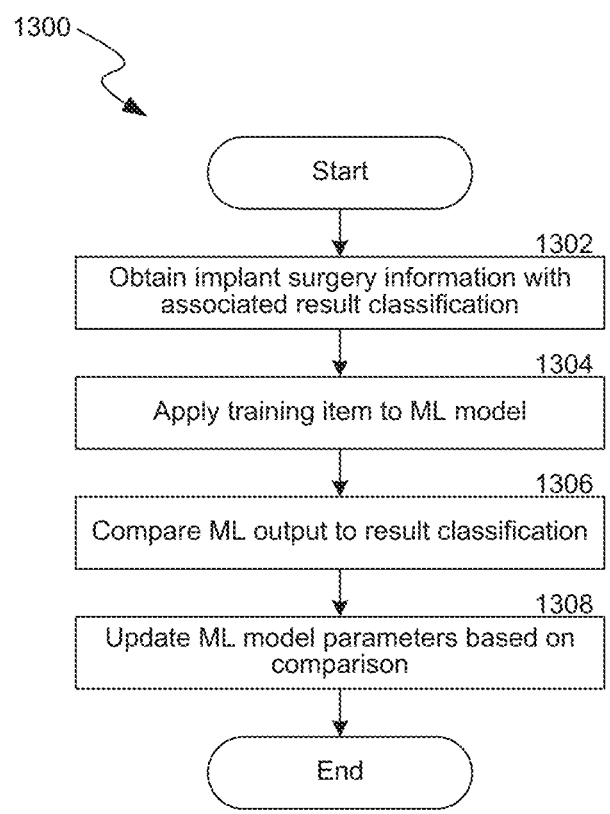
FIG. 13 illustrates a flowchart showing a method for training a machine learning model, according to an embodiment.

FIG. 13 illustrates a flowchart showing a method for training a machine learning model, according to an embodiment. Machine learning models, such as neural networks, can be trained to produce types of results. A neural network can be trained by obtaining, at block 1302, a quantity of "training items," where each training item includes input similar to input the model will receive when in use and a corresponding scored result. At block 1304, the input from each training item can be supplied to the model to produce a result. At block 1306, the result can be compared to the scored result. At block 1308, model parameters can then be updated, based on how similar the model result is to the scored result and/or whether the score is positive or negative.

For example, a model can be trained using sets of preoperative MRI scans of vertebrae paired with pedicle screw placements used in the surgery and corresponding scores for the result of that surgery. The images can be converted to arrays of integers that, when provided to the machine learning model, produce values that specify screw placements. The screw placements can be compared to the actual screw placement used in the surgery that produced the training item. The model parameters can then be adjusted so the model output is more like the screw placement used in the surgery if the surgery was a success or less like the screw placement used in the surgery if the surgery was a failure. The amount of adjustment to the model parameters can be a function of how different the model prediction was from the actual screw configuration used and/or the level of success or failure of the surgery.

As discussed above, machine learning models for the surgical assistance system can be trained to produce various results such as: to directly produce implant configurations upon receiving implant surgery information, to refine implant design, to identify particular vertebral pedicles in various images, to determine an order or subset of images for processing, to localize and classify the target within an image, to segment target vertebrae, to determine boundaries or other features, to localize insertion points, etc.

In various implementations, the training data for a machine learning model can include input data such as medical imaging data, other patient data, or surgeon data. For example, model input can include images of the patient, patient sex, age, height, weight, type of pathology, occupation, activity level, etc., specifics of implant systems (e.g., types and dimensions), availability of available implants, or aspects of a surgeon's preoperative plan (e.g., surgeon's initial implant configuration, detection and measurement of the patient's anatomy on images, etc.). In some implementations, model training data input can include surgeon specifics, such as statistics or preferences for implant configurations used by the surgeon performing the implant surgery or outcomes for implant usages. For example, surgeons may have better skill or experience with particular implant configurations, and the system can be trained to select implant configurations the particular surgeon is more likely to use successfully. The training data input can be paired with results to create training items. The results can be, for example, human annotated medical imaging data (as a comparison for identifications such as boundaries and insertion points identified by a model), human feedback to model outputs, surgeons' post-operative suggestion feedback (e.g., whether the surgeon accepted model provided recommendations completely, or made certain changes, or disregarded), surgeons post-operative operation outcome success score, post-operative images that can be analyzed to determine results, the existence of certain positive or negative patient results, such as cortical breaches or other complications that might have occurred in the procedure, overall level of recovery, or recovery time.

The training data for the machine learning model can be provided for other types of procedures. Training data for a percutaneous procedure can be modified to include, among other things, surgeon specifics for the procedure. For example, the surgeon can input parameters for a desired percutaneous delivery path. The machine learning model can determine appropriate tools and suggestions based on the proposed delivery path. If the machine learning model determines that another delivery path is more suitable based on criteria (including criteria from the surgeon), the training model can indicate that an alternative procedure can be performed. The desired results provided to the training model can vary between percutaneous procedures, open procedures, combinations thereof, or the like.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Except as described herein, the embodiments, features, systems, devices, materials, methods and techniques described herein may, in some embodiments, be similar to any one or more of the embodiments, features, systems, devices, materials, methods and techniques described in U.S. application Ser. No. 16/048,167, filed on Jul. 27, 2017, titled "SYSTEMS AND METHODS FOR ASSISTING AND AUGMENTING SURGICAL PROCEDURES," and U.S. Provisional Patent Application No. 62/537,869, filed on Jul. 27, 2017 titled "SYSTEMS AND METHODS OF PROVIDING ASSISTANCE DURING A SPINAL SURGERY," which are herein incorporated by reference in their entireties. In addition, the embodiments, features, systems, devices, materials, methods and techniques described herein may, in certain embodiments, be applied to or used in connection with any one or more of the embodiments, features, systems, devices, materials, methods and techniques disclosed in the incorporated references.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A non-transitory computer-readable storage medium storing instructions that, when executed by a computing system, cause the computing system to perform operations comprising:
    receiving diagnostic data of a patient, the diagnostic data including image data of the patient's spine;
    analyzing the diagnostic data to identify one or more spinal segments for a surgery to be performed;
    using at least one trained machine learning model to design, based on the one or more areas of interests and/or the diagnostic data, a first patient-specific implant and a second patient-specific implant configured to be spaced apart from the first patient-specific implant when implanted at the one or more spinal segments, wherein designing the first patient-specific implant and the second patient-specific implant includes specifying a first configuration of the first patient-specific implant and a second configuration of the second-patient specific implant;
    generating a virtual model of the first patient-specific implant and the second patient-specific implant; and
    converting the virtual model into 3D fabrication data for manufacturing the first patient-specific implant and the second patient-specific implant.

2. The computer-readable storage medium of claim 1, wherein the operations further comprise causing the 3D fabrication data to be sent to at least one manufacturing system configured to manufacture the first patient-specific implant and the second patient-specific implant.

3. The computer-readable storage medium of claim 1, wherein the first patient-specific implant and/or the second patient specific implant includes at least one of a patient-specific cage, plate, or disk.

4. The computer-readable storage medium of claim 1, wherein the operations further comprise generating patient-specific surgical information for performing the surgery, wherein the patient-specific surgical information includes position information for delivering the first patient-specific implant and the second patient-specific implant to a site within the patient.

5. The computer-readable storage medium of claim 1, wherein the operations further comprise:
   training the at least one machine learning model based on a set of patient data; and
   generating the virtual model of the first patient-specific implant and the second patient-specific implant using another machine learning model.

6. The computer-readable storage medium of claim 1, wherein the operations further comprise:
   determining patient-specific surgical information for performing the surgery; and
   performing one or more structural analyses based on the virtual model of the first patient-specific implant and the second patient-specific implant to determine additional patient-specific surgical information.

7. A non-transitory computer-readable storage medium storing instructions that, when executed by a computing system, cause the computing system to perform operations comprising:
   receiving diagnostic data of a patient;
   analyzing the diagnostic data to identify a spinal segment for a surgery to be performed, the spinal segment including at least a first vertebral level and a second vertebral level;
   using at least one trained machine learning model to design, based on the spinal segment and/or the diagnostic data, a first patient-specific implant configured to be implanted at the first vertebral level and a second patient-specific implant configured to be implanted at the second vertebral level, wherein
      the first patient-specific implant includes a first patient-specific cage, plate, or disk,
      the second patient-specific implant includes a second patient-specific cage, plate, or disk, and
      the first patient-specific implant and the second patient-specific implant are configured to provide a target correction to the spinal segment when implanted in the patient;
   generating a virtual model of the first patient-specific implant and the second patient-specific implant; and
   converting the virtual model into 3D fabrication data for manufacturing the first patient-specific implant and the second patient-specific implant.

8. The computer-readable storage medium of claim 7, wherein the first patient-specific implant includes a first patient-specific cage and wherein the second patient-specific implant includes a second patient-specific cage.

9. The computer-readable storage medium of claim 7, wherein analyzing the diagnostic data includes:
   segmenting the spinal segment; and
   analyzing the segmented spinal segment to determine boundaries of the first vertebral level and the second vertebral level.

10. The computer-readable storage medium of claim 7, wherein the operations further comprise:
    receiving user feedback on the first patient specific implant and/or the second patient specific implant before converting the virtual model into 3D fabrication data; and
    adjusting one or more characteristics of the first patient-specific implant and/or the second patient-specific implant based at least in part on the user feedback and before converting the model into 3D fabrication data.

11. The computer-readable storage medium of claim 7, wherein the operations further comprise:
    performing a finite element analysis on the virtual model of the first patient-specific implant and the second patient-specific implant; and
    adjusting one or more characteristics the first patient-specific implant and/or the second patient-specific implant based on the finite element analysis and before converting the model into 3D fabrication data.

12. The computer-readable storage medium of claim 7, wherein the virtual model is a first virtual model, the method further comprising:
    generating a second virtual model based on the diagnostic data, the second virtual model including at least the spinal segment including the first vertebral level and the second vertebral level,
    wherein analyzing the diagnostic data to identify a spinal segment for surgery includes analyzing the second virtual model.

13. The computer-readable storage medium of claim 12, further comprising combining the first virtual model and the second virtual model to display a virtual representation of the first patient specific implant and the second patient specific implant implanted in the patient.

14. The computer-readable storage medium of claim 7, wherein the at least one trained machine learning model includes a first trained machine learning model, and wherein analyzing the diagnostic data to identify the spinal segment for the surgery to be performed includes using at least a second trained machine learning model.

15. A non-transitory computer-readable storage medium storing instructions that, when executed by a computing system, cause the computing system to perform operations comprising:
    receiving diagnostic data of a patient;
    analyzing the diagnostic data to identify a section of the patient's spine for surgical correction, the section of the patient's spine including at least a first vertebra and a second vertebra;
    using at least one trained machine learning model to design, based on the identified section of the patient's spine and/or the diagnostic data, a first patient-specific implant configured to contact the first vertebra and a second patient-specific implant configured to contact the second vertebra, wherein designing the first patient-specific implant and the second patient-specific implant includes specifying a first configuration of the first patient-specific implant and a second configuration of the second-patient specific implant;
    generating a virtual model of the first patient-specific implant and the second patient-specific implant; and
    manufacturing the first patient-specific implant and the second patient-specific implant.

16. The computer-readable storage medium of claim 15, wherein the first patient-specific implant includes at least one of a patient-specific cage, plate, rod, disk, guide, or screw, and wherein the second patient-specific implant includes at least one of a patient-specific cage, plate, rod, disk, guide, or screw.

17. The computer-readable storage medium of claim 15, wherein analyzing the diagnostic data includes:
   segmenting the identified section of the patient's spine; and
   analyzing the segmented section to determine boundaries of the first vertebra and the second vertebra.

18. The computer-readable storage medium of claim 15, wherein the operations further comprise:
   receiving user feedback on the first patient specific implant and/or the second patient implant before manufacturing the first patient-specific implant and the second patient-specific implant; and
   adjusting one or more characteristics of the first patient-specific implant and/or the second patient-specific implant based at least in part on the user feedback and before manufacturing the first patient-specific implant and the second patient-specific implant.

19. The computer-readable storage medium of claim 15, wherein the operations further comprise:
   performing a finite element analysis of the first patient-specific implant and the second patient-specific implant based on the virtual model; and
   adjusting one or more characteristics the first patient-specific implant and/or the second patient-specific implant based on the finite element analysis and before manufacturing the first patient-specific implant and the second patient-specific implant.

20. The computer-readable storage medium of claim 15, wherein the first patient-specific implant includes a first patient-specific cage, plate, or disk, and wherein the second patient-specific implant includes a second patient-specific cage, plate, or disk.

21. The computer-readable storage medium of claim 15, wherein the virtual model is a first virtual model, the method further comprising:
   generating a second virtual model of at least the spinal segment including the first vertebral level and the second vertebral level based on the diagnostic data,
   wherein analyzing the diagnostic data to identify a spinal segment for surgery includes analyzing the second virtual model.

22. The computer-readable storage medium of claim 21, further comprising combining the first virtual model and the second virtual model to display a virtual representation of the first patient specific implant and the second patient specific implant implanted in the patient.

23. The computer-readable storage medium of claim 15, wherein the at least one trained machine learning model includes a first trained machine learning model, and wherein analyzing the diagnostic data to identify the spinal segment for the surgery to be performed includes using at least a second trained machine learning model.

* * * * *